(12) United States Patent
Sakata et al.

(10) Patent No.: US 6,528,504 B2
(45) Date of Patent: Mar. 4, 2003

(54) OXAZEPINE DERIVATIVES AND MEDICINE CONTAINING THE SAME

(75) Inventors: Katsutoshi Sakata, Kawasaki (JP); Takashi Tsuji, Kawasaki (JP); Noriko Sasaki, Kawasaki (JP); Kazuyoshi Takahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/899,928

(22) Filed: Jul. 9, 2001

(65) Prior Publication Data

US 2002/0099047 A1 Jul. 25, 2002

Related U.S. Application Data

(63) Continuation of application No. PCT/JP00/00071, filed on Jan. 11, 2000.

(30) Foreign Application Priority Data

Jan. 8, 1999 (JP) ............................................ 11-003268
Jan. 8, 1999 (JP) ............................................ 11-003269
Jan. 8, 1999 (JP) ............................................ 11-003270

(51) Int. Cl.[7] ........................... A61K 31/55; A61P 1/00; C07D 267/02
(52) U.S. Cl. .................. 514/211.11; 540/550
(58) Field of Search ...................... 514/211.11; 540/550

(56) References Cited

U.S. PATENT DOCUMENTS 3,454,598 A   7/1969   Yale et al. .................. 260/333
6,127,361 A * 10/2000  Tanaka et al. .......... 514/211.11

FOREIGN PATENT DOCUMENTS

| EP | 0 404 359 | 12/1990 |
|---|---|---|
| EP | 0 889 043 | 1/1999 |
| EP | 1 020 466 | 7/2000 |
| FR | 2 128 097 | 10/1972 |
| WO | WO97/33885 | 9/1997 |
| WO | WO99/12925 | 3/1999 |

* cited by examiner

*Primary Examiner*—Brenda Coleman
(74) *Attorney, Agent, or Firm*—Oblon, Spivak, McClelland, Maier & Neustadt, P.C.

(57) ABSTRACT

The present invention provides (R)-5,11-dihydro-5-[1-(4-methoxyphenethyl)piperidine-2-ylmethyl]dibenzo[b,e][1,4]oxazepine, (R)-5,11-dihydro-5-[1-(4-dimethylaminophenethyl)piperidine-2-ylmethyl]dibenzo[b,e][1,4]oxazepine, compounds analogous to them and pharmaceutical compositions containing such a compound. These compounds are useful for treating or preventing abnormal motor functions of gastrointestinal tracts, particularly irritable bowel syndrome.

18 Claims, No Drawings

OXAZEPINE DERIVATIVES AND MEDICINE CONTAINING THE SAME

This application is a continuation of PCT/JP00/00071 filed Jan. 11, 2000.

BACKGROUND OF THE INVENTION

The present invention relates to 5,11-dihydrodibenzo[b,e][1,4]oxazepine derivatives antagonistic to calcium channel and useful for treating or preventing abnormal motor functions of gastrointestinal tracts, particularly intestinal diseases such as irritable bowel syndrome, stereoisomers thereof, pharmacologically acceptable salts thereof or hydrates thereof, and pharmaceutical compositions containing them as active ingredients.

It is disclosed in, for example, European Patent No. 0404359A1 that 5,11-dihydrodibenzo[b,e][1,4]thiazepine derivatives are usable as calcium channel antagonists selectively effective on gastrointestinal tracts. Quinn, P. et al., Brit. J. Pharmacol. 1994, 112 (Suppl.), Abst 573P and Wallis R. M. et al. Brit. J. Pharmacol. 1994, 112 (Suppl.), Abst. 574P disclose that (S)-5-[[1-(4-methoxyphenyl)ethyl]pyrrolidine-2-ylmethyl]-5,11-dihydrodibenzo[b,e][1,4]thiazepine maleate which is one of derivatives of those compounds has effects similar to the effects of them. Further, International Patent No. 9733885A1 discloses 5-(2-pyrrolidinyl-methyl)-5,11-dihydrodibenzo [b,e][1,4]oxazepine derivatives as medicines for improving motor insufficiency of gastrointestinal tracts. However, the activity and selectivity of these compounds toward gastrointestinal tracts are yet insufficient, and another defect of them is that they have an anticholinergic effect which causes side effects such as thirstiness and mydriasis.

As social environments have been complicated recently, many of people feel the severe stress and patients with irritative bowel syndrome having cardinal symptoms of irregular bowel movement and abdominal pain are increasing in number. Medicines used for improving these diseases are, for example, cholinergic blocking agents, laxatives, antidiarrheal agents, intestinal drugs, mucosal paralyzers, gastrointestinal function regulators, autonomic nerve regulators, Chinese medicines, anxiolytic agents, antidepressant agents, sleep promoting drugs and neurotropic agents. However, the clinical effects of these medicines are yet insufficient and, in addition, they are not always satisfactory from the viewpoint of side effects of them. Under these circumstances, the development of medicines of a new type for improving the gastrointestinal function regulators, which have no side effect, is demanded.

DISCLOSURE OF THE INVENTION

The object of the present invention is to provide new compounds having an excellent effect of improving the gastrointestinal function.

Another object of the present invention is to provide a pharmaceutical composition containing the new compound.

Calcium channel antagonists having an effect of inhibiting the smooth muscle contraction are effective against diseases caused by an abnormal acceleration of contraction of intestinal tracts such as intestinal diseases, e.g. irritative bowel syndrome. In fact, it was reported that calcium channel antagonists such as nicardipine and verapamil are effective against irritative bowel syndrome [Am. J. Gastroenterol., 80, 317 (1985), Gut, 28, 1609 (1987), J. Clin. Psychiatry, 48, 388 (1987) and Pharmacol. Ther., 60, 121 (1993)]. However, the calcium channel antagonists are scarcely used for the clinical treatment because of the main effect of them on the cardiovascular system. Under these circumstances, the inventors made intensive investigations on the development of calcium channel antagonists selective to the intestinal tracts but having only a low toxicity or in other words, ineffective on cardiovascular system for the purpose of obtaining therapeutic agents for intestinal diseases such as abnormal motor functions of gastrointestinal tracts, particularly irritable bowel syndrome. After the investigations, the inventors have found that compounds represented by following general formula [Ia], [Ib] or [Ic] have calcium channel antagonistic activity selective to the intestinal tracts and, therefore, they are effective as agents for regulating gastrointestinal function. The present invention has been completed on the basis of this finding. These compounds have excellent pharmacological effects and, in addition, they are highly soluble in water. It is expected, therefore, that when they are orally administered, they are rapidly absorbed well. It is also expected that when they are used in the form of a liquid preparation, the production of the preparation is easy.

Namely, the present invention relates to 5,11-dihydrodibenzo[b,e][1,4]oxazepine derivatives of following general formula [Ia], [Ib] or [Ic], stereoisomers thereof, pharmacologically acceptable salts thereof or hydrates thereof, and pharmaceutical compositions containing them as active ingredients:

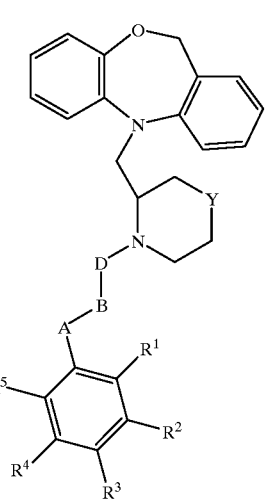

[Ia]

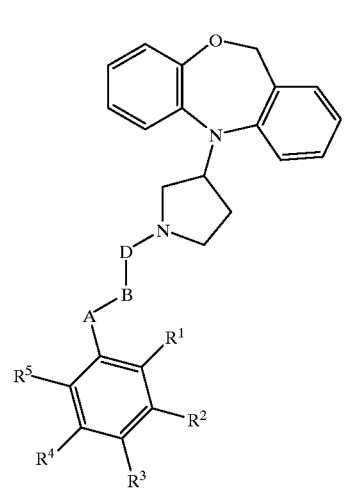

[Ib]

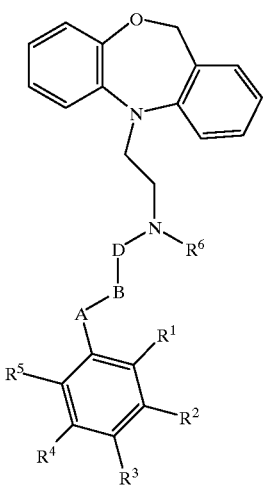

wherein $R^1$ to $R^5$ may be the same or different from each other and they each represent hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —$O(CH_2)_nO$— group (n being 1, 2 or 3), $R^6$ represents hydrogen or a lower alkyl group, Y represents methylene group, oxygen atom, sulfur atom or an alkylamino group, A represents $CH_2$, CHOH, CO or O, B represents $CH_2$, CHOH or CO, or A-B represents CH=CH, and D represents $CH_2$, $CH_2$—$CH_2$ or $CH_2$—$CH_2$—$CH_2$, or B-D represents $CH_2$.

BEST MODE FOR CARRYING OUT THE INVENTION

In $R^1$ to $R^5$ in [Ia], [Ib] and [Ic] in the general formula, the halogen atoms include fluorine atom, chlorine atom, etc., the lower alkyl groups include those having 1 to 5 carbon atoms such as methyl group, ethyl group and n-propyl group, the lower alkoxyl groups include those having 1 to 5 carbon atoms such as methoxyl, ethoxyl and n-propoxyl group, the lower alkylamino groups include monoalkylamino groups and dialkylamino groups, and —$O(CH_2)_nO$— groups include methylenedioxy group, ethylenedioxy group and propylenedioxy group. Among them, the halogen atoms are preferably fluorine atom and chlorine atom, and the lower alkyl groups are preferably those having 1 to 3 carbon atoms. The lower alkoxyl groups are preferably those having 1 to 3 carbon atoms. The monoalkylamino groups and dialkylamino groups are preferably those wherein the alkyl groups have 1 to 5 carbon atoms, more preferably those wherein the alkyl groups have 1 to 3 carbon atoms.

A-B-D is preferably any of $CH_2$—$CH_2$, CO—$CH_2$, CHOH—$CH_2$, CHOH—$CH_2$—$CH_2$, $CH_2$—CHOH—$CH_2$, CH=CH—$CH_2$, CO—$CH_2$—$CH_2$, O—$CH_2$—$CH_2$, $CH_2$—CO—$CH_2$ or $CH_2$—$CH_2$—$CH_2$.

In general formula [Ia] in the present invention, Y is preferably methylene group and $R^1$ to $R^5$ are not hydrogen atoms at the same time. In the present invention, one of $R^1$ to $R^5$ is preferably amino group or a lower alkylamino group and the others are hydrogen atom, or $R^2$ or $R^3$ is a halogen atom, a lower alkyl group or a lower alkoxyl group. It is also preferred that either $R^2$ or $R^3$ or both of $R^2$ and $R^3$ are methoxyl group, or $R^2$ and $R^3$ together form methylenedioxy group, and $R^1$, $R^4$ and $R^5$ are hydrogen atom. It is further preferred that $R^3$ is methoxyl group, and $R^1$, $R^2$, $R^3$, $R^4$ and $R^5$ are each hydrogen atom, Y is methylene group, and A and B-D are $CH_2$. When Y is methylene group, preferably the absolute configuration at the 2-position of the piperidine ring is R-configuration, and when Y is not methylene group, the position thereof in the nitrogen-containing 6-membered ring has a configuration similar to it. In those compounds, examples of particularly preferred compounds are (R)-5,11-dihydro-5-[1-(4-methoxyphenethyl)piperidine-2-ylmethyl]dibenzo [b,e][1,4] oxazepine (Ia-1), (R)-5,11-dihydro-5-[1-(4-dimethylaminophenethyl) piperidine-2-ylmethyl]dibenzo[b,e][1,4]oxazepine (Ia-2), (R)-5,11-dihydro-5-[1-(3-methoxyphenethyl)piperidine-2-ylmethyl] dibenzo [b,e][1,4]oxazepine, (R)-5,11-dihydro-5-[1-[3-(4-methoxyphenyl)propyl]piperidine-2-ylmethyl]dibenzo[b,e] [1,4]oxazepine, (R)-5,11-dihydro-5-[1-(3,4-methylenedioxyphenethyl)piperidine-2-ylmethyl]dibenzo [b,e][1,4] oxazepine and (R)-5-[1-(4-chlorophenethyl) piperidine-2-ylmethyl]-5,11-dihydrodibenzo[b,e][1,4] oxazepine, represented by the following formulae, and pharmacologically acceptable salts and hydrates of them.

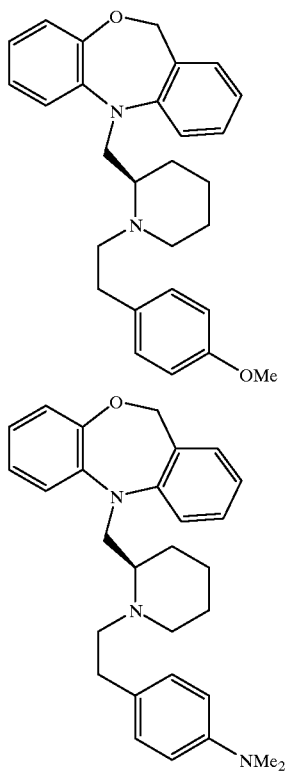

In general formula [Ib], it is preferred in the present invention that $R^1$ to $R^5$ are not hydrogen atoms at the same time. In the present invention, one of $R^1$ to $R^5$ is preferably amino group or a lower alkylamino group and the others are hydrogen atom, or $R^2$ or $R^3$ is a halogen atom, a lower alkyl group or a lower alkoxyl group. It is also preferred that either $R^2$ or $R^3$ or both of $R^2$ and $R^3$ are methoxyl group, or $R^2$ and $R^3$ together form methylenedioxy group, and $R^1$, $R^4$ and $R^5$ are each hydrogen atom. It is further preferred that $R^3$ is methoxyl group, and $R^1$, $R^2$, $R^4$ and $R^5$ are each hydrogen atom. A and B-D both represent $CH_2$. It is also preferred that the absolute configuration at the 3-position of the pyrrolidine ring is R-configuration. In those compounds, examples of particularly preferred compounds are (R)-5,11-dihydro-5-[1-(4-methoxyphenethyl)pyrrolidine-3-yl]dibenzo[b,e][1,4] oxazepine (Ib-1), (R)-5,11-dihydro-5-[1-(4-dimethylaminophenethyl)pyrrolidine-3-yl]dibenzo [b,e][1, 4]oxazepine (Ib-2), (R)-5,11-dihydro-5-[1-[3-(4-methoxyphenyl) propyl]pyrrolidine-3-yl]dibenzo[b,e][1,4]oxazepine, (R)-5,11-dihydro-5-[1-(3,4-methylenedioxyphenethyl)pyrrolidine-3-yl]dibenzo[b,e][1,4]oxazepine and (R)-5-[1-(4-chlorophenethyl)pyrrolidine-3-yl]-5,11-dihydro-dibenzo[b,e][1,4]oxazepine, represented by the following formulae, and pharmacologically acceptable salts and hydrates of them.

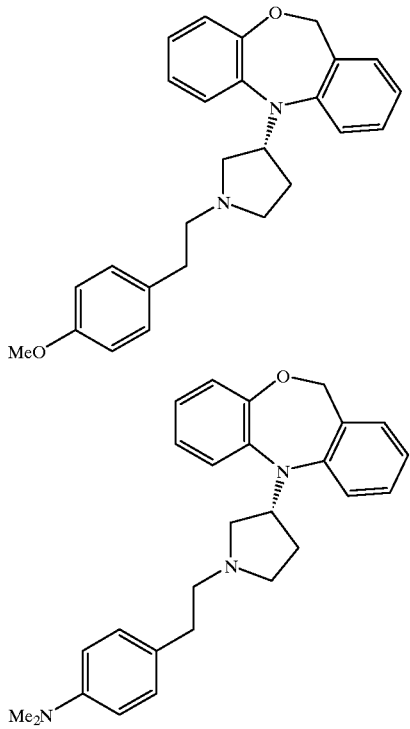

In general formula [Ic], it is preferred in the present invention that $R^6$ is a lower alkyl group having 1 to 3 carbon atoms. Preferably, $R^1$ to $R^5$ are not hydrogen atoms at the same time. In the present invention, one of $R^1$ to $R^5$ is preferably amino group or a lower alkylamino group and the others are each hydrogen atom, or $R^2$ or $R^3$ is a halogen atom, a lower alkyl group or a lower alkoxyl group. It is also preferred that either $R^2$ or $R^3$ or both of $R^2$ and $R^3$ are methoxyl group, or $R^2$ and $R^3$ together form methylenedioxy group, and $R^1$, $R^4$ and $R^5$ are hydrogen atom. It is further preferred that $R^3$ is methoxyl group, and $R^1$, $R^2$, $R^4$ and $R^5$ are each hydrogen atom. $R^6$ is preferably a lower alkyl group having 1 to 3 carbon atoms. In those compounds, examples of particularly preferred compounds are 5,11-dihydro-5-[2-[N-(4-methoxyphenethyl)-N-methyl-amino]ethyl]dibenzo[b,e][1,4]oxazepine (Ic-1), 5,11-dihydro-5-[2-[N-(3-methoxyphenethyl)-N-methylamino]ethyl]dibenzo[b,e][1,4]oxazepine (Ic-2), 5,11-dihydro-5-[2-[N-[3-(4-methoxyphenyl)propyl]-N-methylamino]ethyl]dibenzo[b,e][1,4]oxazepine (Ic-3), 5,11-dihydro-5-[2-[N-methyl-N-(3,4-methylenedioxyphenethyl)amino]ethyl]dibenzo[b,e][1,4]oxazepine (Ic-4), 5-[2-[N-(4-chlorophenethyl)-N-methylamino]ethyl]-5,11-dihydro-dibenzo[b,e][1,4]oxazepine, 5,11-dihydro-5-[2-[N-(4-dimethylamino-phenethyl)-N-methylamino]ethyl]dibenzo[b,e][1,4]oxazepine (Ic-5) and 5,11-dihydro-5-[2-[N-(3-dimethylaminophenethyl)-N-methylamino]ethyl]dibenzo[b,e][1,4]oxazepine represented by the following formulae, and pharmacologically acceptable salts and hydrates of them.

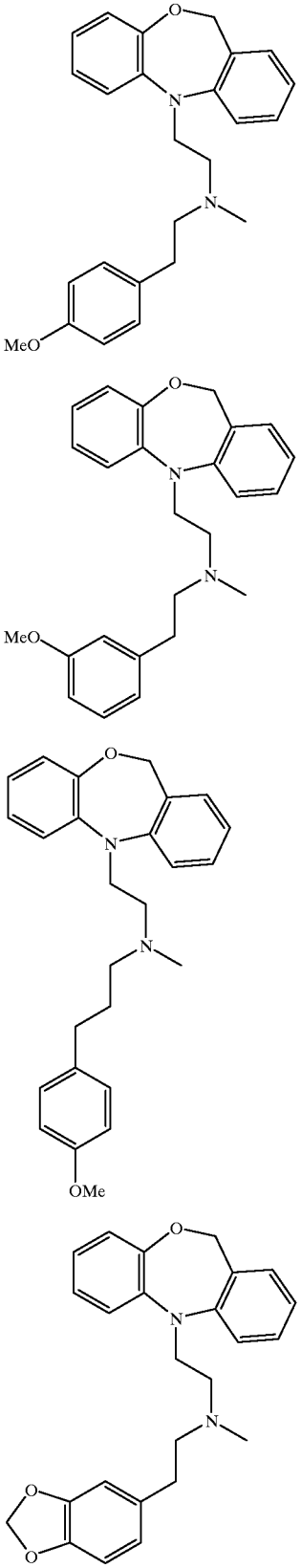

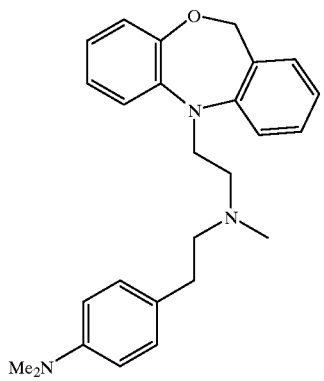

The pharmacologically acceptable salts of the compounds of the present invention are, for example, salts with mineral acids (inorganic acids) such as hydrochloric acid, hydrobromic acid, sulfuric acid and phosphoric acid, and salts with organic acids such as acetic acid, lactic acid, fumaric acid, maleic acid, malic acid, tartaric acid, citric acid, oxalic acid, aspartic acid and methanesulfonic acid. In those salts, the inorganic salts are preferred.

Compounds [Ia] and [Ib] of the present invention have one or more asymmetric carbon atoms and, therefore, there can be optical isomers of them. The optical isomers, mixtures of them and racemic compounds are included in the compounds of the present invention. In those compounds, the configuration at the 2-position of the piperidine ring is preferably R-configuration, and when Y is not methylene group, the configuration is preferably similar to it. The compounds of the present invention and pharmacologically acceptable salts thereof may be in the form of hydrates or solvates thereof. These hydrates or solvates are also included in the present invention.

Compounds [Ia] of the present invention can be produced by, for example, following process A:

A

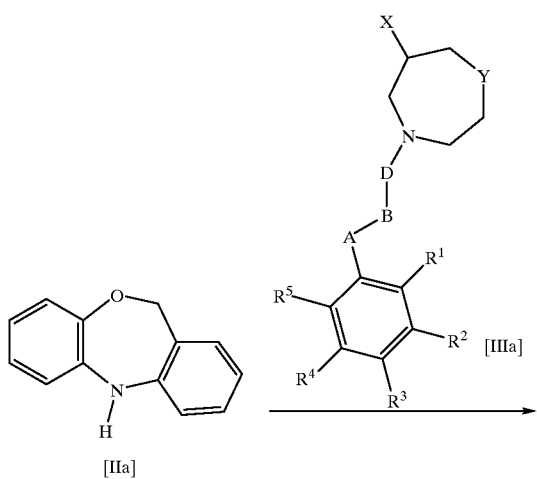

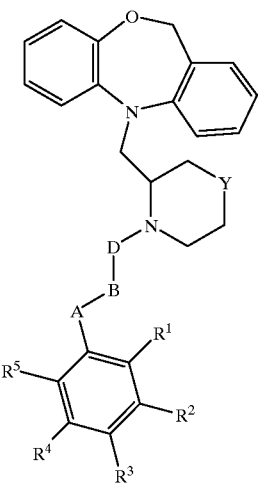

wherein $R^1$ to $R^5$, A, B, D and Y are as defined above, and X represents chlorine atom, bromine atom or iodine atom.

Compounds [Ia] of the present invention can be produced by reacting a compound [IIa] with a halide represented by above general formula [IIIa] in the presence of a base in a solvent.

The reaction solvents suitable for the above-described reaction are dimethyl sulfoxide; amides such as N,N-dimethylformamide; ethers such as tetrahydrofuran, diethyl ether, dioxane and 1,2-dimethoxyethane; acetonitrile; toluene; xylene; benzene and the like. The bases are, for example, sodium carbonate, potassium carbonate, sodium hydride, potassium hydride, lithium diisopropylamide, n-butyl lithium, sodium methoxide and potassium t-butoxide.

The reaction temperature is usually 0 to 150° C., preferably in the range of room temperature to 100° C. The reaction time, which varies depending on the reaction temperature and the variety of the solvent, is usually 1 to 50 hours.

The amounts of compound [IIIa] and the base are 0.5 to 5 molar equivalents, preferably 0.8 to 2 molar equivalents, per molar equivalent of the compound [IIa].

Compounds [IIa] used as the starting material for the above-described reaction can be produced by a publicly known method [J. Med. Chem., 7, 609 (1964)].

The halides of above general formula [IIIa] can be produced by reducing pipecolic acid, 3-morpholinecarboxylic acid or the like to obtain an amino alcohol, N-alkylating the amino alcohol and halogenating the alcohol moiety of the resulting compound with mesyl chloride, tosyl chloride or the like. The ring is enlarged by this process.

Compounds [Ia] of the present invention can be produced by following process B:

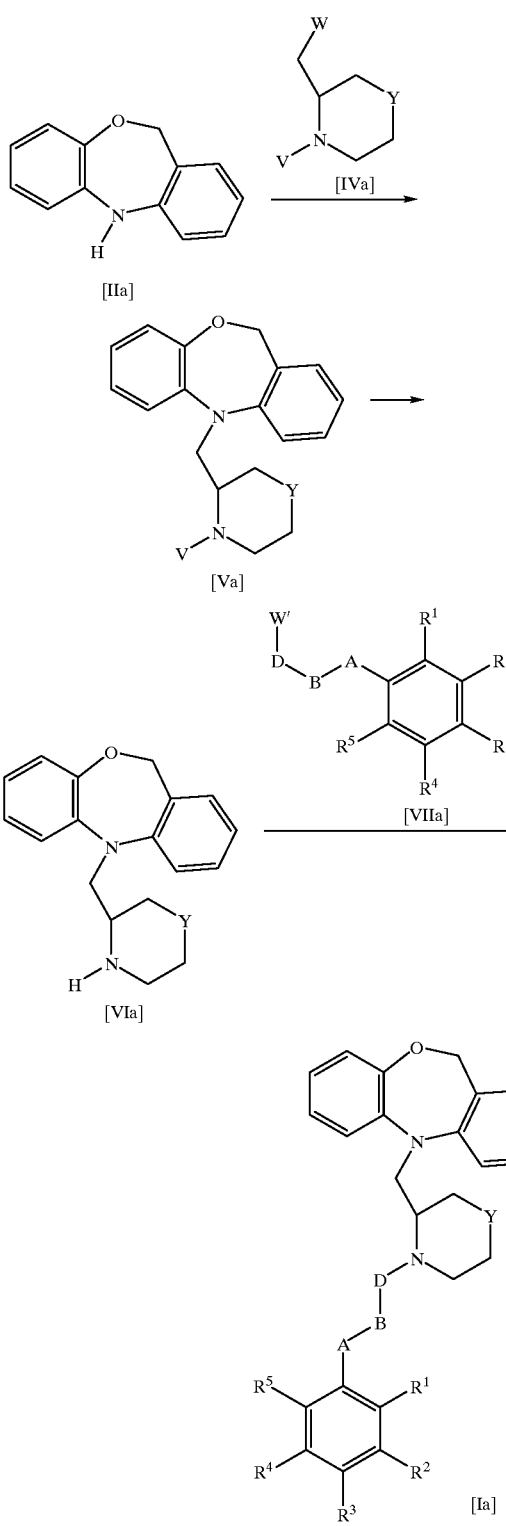

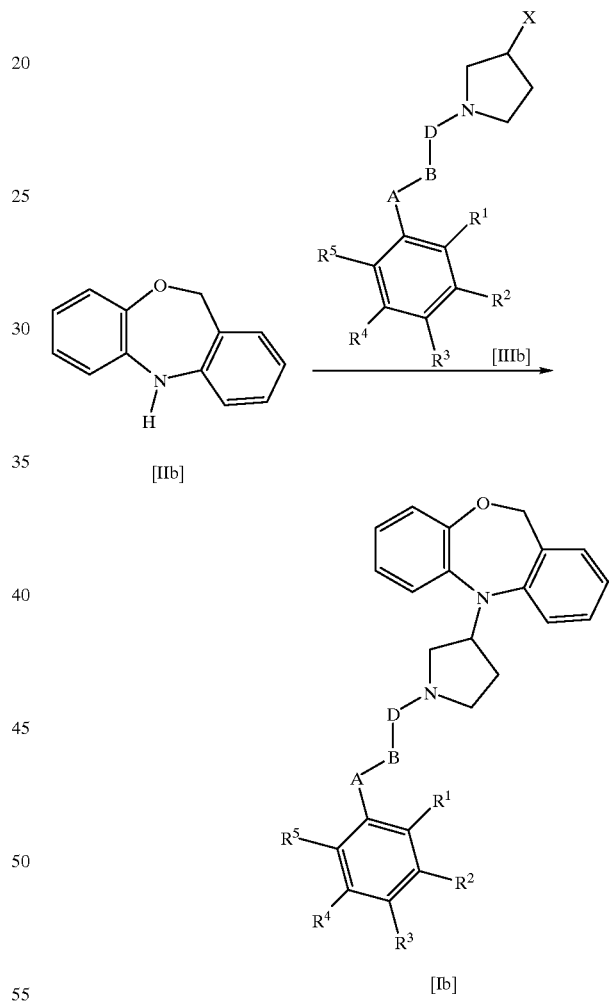

wherein $R^1$ to $R^5$, A, B, D and Y are as defined above, V represents a protective group for amino group such as t-butoxycarbonyl group, benzyloxycarbonyl group or tosyl group, and W and W' each represent a leaving group such as chlorine atom, bromine atom, iodine atom, mesyloxy group or tosyloxy group.

Compounds [Ia] of the present invention can be produced by dropping N-t-butoxycarbonyl-2-piperidylmethyl tosylate of above general formula [IVa] or the like into compound [IIa] in the presence of a base to conduct the reaction and thereby obtaining a compound of general formula [Va], then removing the protective group to obtain a compound of general formula [VIa] and reacting this compound with a compound of general formula [VIIa] in the presence of a base. The solvents and bases used for the reactions for obtaining the compound [Va] from compound [IIa], and compound [Ia] from compound [VIa] may be the same as those usable for above-described reaction A.

Compounds [IVa] can be obtained by reducing pipecolic acid, 3-morpholinecarboxylic acid or the like, protecting an amino group of the obtained amino alcohol and converting the alcohol moiety to a leaving group by an ordinary method.

Compounds [Ib] of the present invention can be produced by, for example, the following process:

wherein $R^1$ to $R^5$, A, B and D are as defined above, and X represents a leaving group such as a halogen atom, tosyloxy group or mesyloxy group.

The solvents suitable for use for the above reaction are dimethyl sulfoxide; amides such as N,N-dimethylformamide, ethers such as tetrahydrofuran, diethyl ether, dioxane and 1,2-dimethoxyethane, acetonitrile, toluene, xylene, benzene and the like. The bases are, for example, sodium carbonate, potassium carbonate, sodium hydride, potassium hydride, lithium diisopropylamide, n-butyllithium, sodium methoxide and potassium t-butoxide.

The reaction temperature is usually 0 to 150° C., preferably in the range of room temperature to 100° C. The reaction time, which varies depending on the reaction temperature and the variety of the solvent, is usually 1 to 50 hours.

The amounts of compound [IIb] and the base are 0.5 to 10 molar equivalents, preferably 0.8 to 5 molar equivalents, per molar equivalent of compound [IIIb].

Compounds [IIb] used as the starting materials for the above-described reaction can be prepared by a publicly known method [J. Med. Chem., 7, 609 (1964)].

Compounds of above general formula [IIIb] can be obtained by N-alkylating 3-hydroxypyrrolidine and then reacting the obtained product with phosphorus oxychloride, thionyl chloride, tosyl chloride, mesyl chloride or the like.

The absolute configuration of pyrrolidine ring varies depending on the absolute structure of 3-hydroxypyrrolidine used as the starting material, and the variety and introduction method of the leaving group. For example, when mesyloxy group or tosyloxy group is used as the leaving group, the steric inversion occurs in the condensation reaction and, therefore, S-compound can be obtained from (R)-3-hydroxypyrrolidine and R-compound can be obtained from (S)-3-hydroxypyrrolidine.

Compounds [Ic] of the present invention can be produced by, for example, the following process:

Namely, a compound [IIc] is converted to a compound of above general formula [IIIc], which is then reacted with a compound of general formula [IVc] in the presence of a base. The reaction solvents suitable for use for the above reaction are dimethyl sulfoxide, amides such as N,N-dimethylformamide, ethers such as tetrahydrofuran, diethyl ether, dioxane and 1,2-dimethoxyethane, acetonitrile, toluene, xylene, benzene and the like. The bases are, for example, sodium carbonate, potassium carbonate, sodium hydride, potassium hydride, lithium diisopropylamide, n-butyllithium, sodium methoxide and potassium t-butoxide.

The reaction temperature is usually 0 to 150° C., preferably in the range of room temperature to 100° C. The reaction time, which varies depending on the reaction temperature and the variety of the solvent, is usually 1 to 50 hours. The amount of the base is at least equimolar to that of compound [IIIc], preferably 1 to 5 mols per mol of compound [IIIc]. The molar ratio of compound [IIIc] to compound [IVvc] is 0.5/1 to 2/1, preferably 0.7/1 to 1.5/1.

Compounds [Ic] of the present invention can be obtained by converting compound [IIc] to a compound of above general formula [Vc] and condensing the obtained compound with compound [VIc] in the presence of a base. The reaction solvent and base used for the condensation reaction can be the same as those in the above-described reaction.

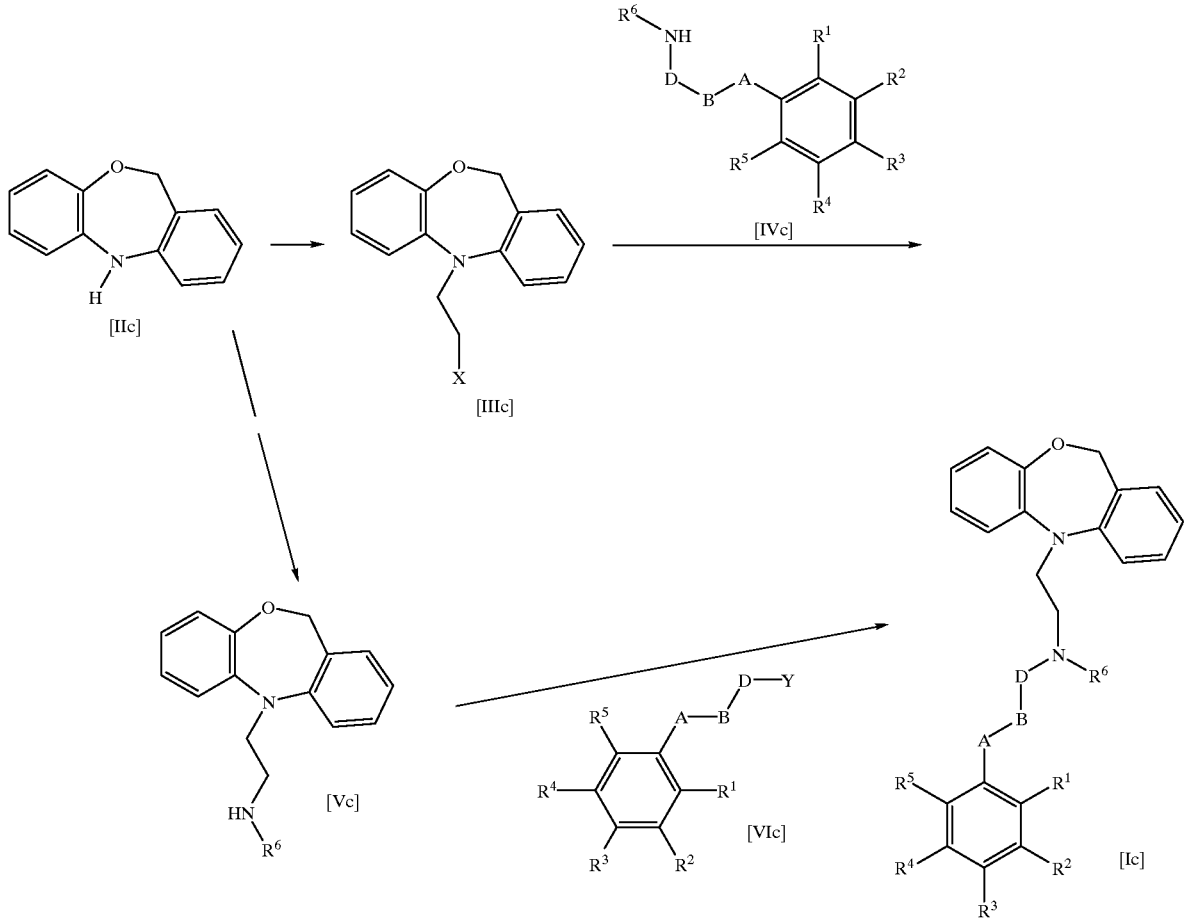

wherein $R^1$ to $R^6$, A, B and D are as defined above, and X and Y each represent a leaving group such as a halogen atom, tosyloxy group or mesyloxy group.

The reaction temperature and the reaction time are also as described above. The amount of the base is at least equimolar to compound [VIc], preferably 1 to 5 mols per mol of compound [VIc]. The molar ratio of compound [Vc] to compound [VIc] is 0.5/1 to 2/1, preferably 0.7/1 to 1.5/1.

Compound [IIc] used as the starting material for the above-described reaction can be prepared by a publicly known method [J. Med. Chem., 7, 609 (1964)]. Compounds [IIIc] can be easily obtained by a combination of known processes. Namely, it can be prepared by alkylating compound [IIc] with a haloacetic ester, reducing the obtained product to obtain an alcohol, converting the hydroxyl group of the alcohol into a leaving group or alkylating compound [IIc] with a 2-haloethanol, in which the hydroxyl group is protected, removing the protective group and converting the hydroxyl group into a leaving group. Compounds [IVc] can be easily obtained by various known methods such as the alkylation reaction of an amine with a corresponding halide, reductive alkylation reaction of an amine with a corresponding aldehyde, and the acylation of an amine with a corresponding carboxylic acid followed by the reduction.

Compounds [Vc] can be easily obtained by various known methods such as the alkylation of compound [IIc] with a haloacetic amide followed by the reduction of the alkylation product, or by the alkylation of compound [IIc] with a haloacetic ester followed by the amidation.

When the compounds of the present invention are used in the form of a pharmaceutical preparation or a pharmaceutical composition, they can be suitably mixed with a pharmaceutically acceptable additive such as an excipient, a carrier or a diluent, and orally or parenterally administered in the form of tablets, capsules, granules, grains, powder, pills, syrup, suspension, emulsion, ointment, suppositories or injection. In the present invention, a pharmaceutical preparation or a pharmaceutical composition containing a compound of the present invention as the active ingredient and a pharmaceutically acceptable carrier and/or diluent is preferred. The carriers and diluents include, for example, glucose, sucrose, lactose, talc, silica, cellulose, methylcellulose, starch, gelatin, ethylene glycol, polyethylene glycol, glycerol, ethanol, water and oils and fats.

The dose and dosage of the compounds of the present invention are suitably variable depending on the variety of the disease, age, body weight, etc. of the patient. For example, when the compounds of the present invention are orally administered for treating intestinal diseases, such as irritable bowel syndrome, about 0.1 to 1,000 mg/day/adult thereof is given at once or in several portions.

EXAMPLES

The following Examples, Test Examples and Preparation Examples will further illustrate the present invention, which by no means limit the invention, within the gist of the invention.

Example 1

(R)-5,11-Dihydro-5-[1-(4-methoxyphenethyl) piperidine-2-ylmethyl]dibenzo[b,e][1,4]oxazepine Hydrochloride (R)-2-Hydroxymethyl-1-(4-methoxyphenethyl)piperidine:

(R)-2-hydroxymethylpiperidine [prepared by a process described in Japanese Patent Unexamined Published Application (hereinafter referred to as "J. P. KOKAI") No. Sho 48-19597] (600 mg, 5.22 mmol), 4-methoxyphenethyl tosylate (1.76 g, 5.74 mmol), sodium carbonate (608 mg, 5.74 mmol) and sodium iodide (100 mg, 0.67 mmol) were added to acetonitrile (50 ml), and they were heated under reflux at 90° C. for 3.5 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with hexane and dichloromethane (1:1), then with dichloromethane and finally with dichloromethane and methanol (20:1). The appropriate fractions were combined, and the solvent was evaporated under reduced pressure to obtain (R)-2-hydroxymethyl-1-(4-methoxyphenethyl) piperidine in the form of a light yellow oil (617 mg, 47%).

NMR (CDCl$_3$) δ: 1.38–1.76 (6H, m), 2.36–2.52(2H, m), 2.63–2.75 (3H, m). 2.91–2.99 (1H, m), 3.04–3.12 (1H, m), 3.41–3.50 (1H, m), 3.71–3.78 (1H, m) 3.80 (3H, s) 6.83 (2H, d, J=8.7 Hz), 7.11 (2H, d, J=8.7 Hz)

(R)-3-Chloro-1-(4-methoxyphenethyl)homopiperidine (R)-2-Hydroxymethyl-1-(4-methoxyphenethyl)piperidine (617 mg) was dissolved in 10 ml of dichloromethane. Triethylamine (0.30 g, 2.7 mmol) and methanesulfonyl chloride (0.30 g, 2.6 mmol) were added to the obtained solution under stirring under cooling on ice. They were stirred under cooling on ice for 1 hour and then at room temperature for 4 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-(4-methoxyphenethyl)homopiperidine in the form of a light yellow oil (632 mg, 97%).

NMR (CDCl$_3$) δ: 1.30–1.44 (1H, m), 1.56–1.75 (5H, m), 2.38–2.47 (1H, m), 2.60–2.79 (4H, m), 2.83–2.97 (2H, m), 3.60 (1H, dd, J=3.7, 12.7 Hz), 3.66 (1H, dd, J=7.0, 12.7 Hz), 3.79 (3H, s), 6.83 (2H, d, J=9.3 Hz), 7.10 (2H, d, J=9.3 Hz)

(R)-5,11-Dihydro-5-[1-(4-metoxyphenethyl)piperidine-2-ylmethyl]dibenzo [b,e][1,4]oxazepine 60% Sodium hydride (88 mg, 2.2 mmol) was washed with hexane under argon atmosphere, and then suspended in dimethyl sulfoxide (10 ml). The obtained suspension was stirred at room temperature for 30 minutes. 5,11-Dihydrodibenzo[b,e][1,4]oxazepine (0.40 g, 2 mmol) was added to the suspension, and they were stirred at room temperature for 30 minutes and then at 50° C. for 30 minutes. A solution of (R)-3-chloro-1-(4-methoxyphenethyl)homopiperidine (0.59 g, 2.2 mmol) in dimethyl sulfoxide (5 ml) was added dropwise into the obtained solution, and they were stirred at 50° C. for 2 hours. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (6:1) and then with hexane and ethyl acetate (3:1). The appropriate fractions were combined, and the solvent was evaporated under reduced pressure to obtain (R)-5,11-dihydro-5-[1-(4-methoxyphenethyl) piperidine-2-ylmethyl] dibenzo[b,e][1, 4]oxazepine in the form of a light yellow solid (0.63 g, 73%).

NMR (CDCl$_3$) δ: 1.23–1.84 (6H, m), 2.26–2.34 (1H, m), 2.54–2.72 (4H, m), 2.88–3.06 (2H, m), 3.65 (1H, dd, J=7.7, 15.0 Hz), 3.79 (3H, s), 4.04 (1H, dd, J=5.0, 15.0 Hz), 5.13 (1H, d, J=13.0 Hz), 5.21 (1H, d, J=13.0 Hz), 6.77–6.86 (5H, m), 6.95–7.10 (5H, m), 7.22–7.33 (2H, m)

(R)-5,11-Dihydro-5-[1-(4-methoxyphenethyl)piperidine-2-ylmethyl] dibenzo[b,e][1,4]oxazepine Hydrochloride 3.0 ml of 4 M hydrochloric acid/dioxane was added to a solution of (R)-5,11-dihydro-5-[1-(4-methoxyphenethyl) piperidine-2-ylmethyl] dibenzo[b,e][1,4]oxazepine (0.63 g) in dichloromethane (10 ml), and they were stirred for 2 hours. The solvent was evaporated under reduced pressure. The obtained residue was recrystallized from a mixed solvent of acetone and ether to obtain the title compound in the form of a white solid (496 mg, 73%).

Melting point: 199–201° C.
ESI/Mass: 429 [M+H$^+$]
NMR (CD$_3$OD) δ: 1.23–1.84 (6H, m), 2.26–2.34 (1H, m), 2.54–2.72 (4H, m), 2.88–3.06 (2H, m), 3.65 (1H, dd, J=7.7, 15.0 Hz), 3.79 (3H, s), 4.04 (1H, dd, J=5.0, 15.0 Hz), 5.13 (1H, d, J=13.0 Hz), 5.21 (1H, d, J=13.0 Hz), 6.77–6.86 (5H, m), 6.95–7.10 (5H, m), 7.22–7.33 (2H, m)

Example 2

(S)-5,11-Dihydro-5-[1-(4-methoxyphenethyl) piperidine-2-ylmethyl] dibenzo[b,e][1,4]oxazepine Hydrochloride The title compound was obtained in the same manner as that of Example 1 except that (R)-2-hydroxymethylpiperidine was replaced with (S)-2-hydroxymethylpiperidine. ESI-MS and NMR spectrum of this compound were the same as those of the compound of Example 1.

Melting point: 197–199° C.

Example 3

(R)-5,11-Dihydro-5-[1-(3-methoxyphenethyl) piperidine-2-ylmethyl] dibenzo[b,e][1,4]oxazepine Hydrochloride (R)-2-Hydroxymethyl-1-(3-methoxyphenethyl)piperidine (R)-2-hydroxymethylpiperidine (288 mg, 2.50 mmol), 3-methoxyphenethyl mesylate (863 mg, 3.75 mmol), sodium carbonate (398 mg, 3.75 mmol) and sodium iodide (30 mg, 0.20 mmol) were added to acetonitrile (25 ml), and they were heated under reflux at 90° C. for 6 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with dichloromethane and then with dichloromethane and methanol (20:1). The appropriate fractions were combined, and the solvent was evaporated under reduced pressure to obtain (R)-2-hydroxymethyl-1-(3-methoxyphenethyl) piperidine in the form of a light yellow oil (322 mg, 52%).

NMR (CDCl$_3$) δ:1.34–1.77 (6H, m), 2.31–2.63 (4H, m), 2.68–2.84 (1H, m). 2.94–3.10 (2H, m), 3.43–3.51 (1H, m), 3.71–3.77 (1H, m), 3.81 (3H, s) 6.74-6.85 (3H, m), 7.19–7.26 (1H, m)

(R)-3-Chloro-1-(3-methoxyphenethyl)homopiperidine (R)-2-Hydroxymethyl-1-(3-methoxyphenethyl)piperidine (322 mg, 1.28 mmol) was dissolved in 10 ml of dichloromethane. Triethylamine (170 mg, 1.68 mmol) and methanesulfonyl chloride (192 mg, 1.68 mmol) were added to the obtained solution under stirring under cooling on ice. They were stirred under cooling on ice for 1 hour and then at room temperature for 18 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-(3-methoxyphenethyl)homopiperidine in the form of a light yellow oil (182 mg, 53%).

NMR (CDCl$_3$) δ: 1.30–1.44 (1H, m), 1.56–1.74 (5H, m), 2.39–2.47 (1H, m), 2.62–2.81 (4H, m), 2.84–2.96 (2H, m), 3.61 (1H, dd, J=3.7, 12.7 Hz), 3.67 (1H, dd, J=7.0, 12.7 Hz), 3.81 (3H, s), 6.72–6.80 (3H, m), 7.17 (1H, m) (R)-5,11-Dihydro-5-[1-(3-methoxyphenethyl)piperidine-2-ylmethyl] dibenzo[b,e][1,4]oxazepine:

60% Sodium hydride (27 mg, 0.68 mmol) was washed with hexane under argon atmosphere, and then suspended in dimethyl sulfoxide (5 ml). The obtained suspension was stirred at room temperature for 30 minutes. 5,11-Dihydrodibenzo[b,e][1,4]oxazepine (122 mg, 0.68 mmol) was added to the suspension, and they were stirred at room temperature for 20 minutes and then at 50° C. for 30 minutes. A solution of (R)-3-chloro-1-(3-methoxyphenethyl)homopiperidine (182 mg, 0.68 mmol) in dimethyl sulfoxide (3 ml) was added dropwise into the obtained solution, and they were stirred at 50° C. for 150 minutes. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (10:1) and then with hexane and ethyl acetate (4:1). The appropriate fractions were combined, and the solvent was evaporated under reduced pressure to obtain (R)-5,11-dihydro-5-[1-(3-methoxyphenethyl)piperidine-2-ylmethyl] dibenzo[b,e][1, 4]oxazepine in the form of a light yellow oil (78 mg, 30%).

NMR (CDCl$_3$) δ: 1.37–1.80 (6H, m), 2.16–2.44 (1H, m), 2.50–2.70 (3H, m), 2.73–2.83 (1H, m), 2.90–3.03 (2H, m), 3.56–3.69 (1H, m), 3.78 (3H, s), 3.98–4.08 (1H, m), 5.12 (1H, d, J=13.3 Hz), 5.21 (1H, d, J=13.3 Hz), 6.68–6.72 (4H, m), 6.95–7.08 (4H, m), 7.15–7.32 (4H, m)

(R)-5,11-Dihydro-5-[1-(4-methoxyphenethyl)piperidine-2-ylmethyl] dibenzo[b,e][1,4] oxazepine Hydrochloride 0.5 ml of 4 M hydrochloric acid/ethyl acetate was added to a solution of (R)-5,11-dihydro-5-[1-(4-methoxyphenethyl)piperidine-2-ylmethyl]dibenzo[b,e][1,4] oxazepine (78 mg) in dichloromethane (5 ml), and they were stirred for 2 hours. The solvent was evaporated under reduced pressure. The title compound was obtained in the form of a light yellow solid (75 mg, 90%).

ESI/Mass: 429 [M+H$^+$]
NMR (CD$_3$OD) δ: 1.40–1.95 (6H, m), 2.55–2.65 (1H, m), 2.75–3.15 (4H, m), 3.45–3.60 (1H, m), 3.74 (3H, s), 3.95–4.14 (2H, m), 4.19 (1H, b), 5.21 (1H, d, J=14.0 Hz), 5.27 (1H, d, J=14.0 Hz), 6.60–6.92 (5H, m), 7.00–7.41 (7H, m)

Example 4

(R)-5,11-Dihydro-5-[1-[3-(4-methoxyphenyl)propyl] piperidine-2-ylmethyl]dibenzo[b,e][1,4]oxazepine Hydrochloride (R)-2-Hydroxymethyl-1-[3-(4-methoxyphenyl)propyl] piperidine (R)-2-hydroxymethylpiperidine (288 mg, 2.50 mmol), 3-(4-methoxyphenyl)propyl mesylate (915 mg, 3.75 mmol), sodium carbonate (398 mg, 3.75 mmol) and sodium iodide (30 mg, 0.20 mmol) were added to acetonitrile (25 ml), and they were heated under reflux at 90° C. for 6 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with dichloromethane as the eluent and then with dichloromethane and methanol (20:1). The appropriate fractions were combined, and the solvent was evaporated under reduced pressure to obtain (R)-2-hydroxymethyl-1-[3-(4-methoxy-phenyl) propyl] piperidine in the form of a light yellow oil (422 mg, 64%).

NMR (CDCl$_3$) δ: 1.29–1.73 (6H, m), 1.81 (2H, q, J=8.3 Hz), 2.28–2.37 (1H, m), 2.43–2.63 (3H, m). 2.75–2.86 (1H, m), 2.90–3.06 (2H, m), 3.47 (1H, dd, J=4.3, 12.0 Hz), 3.73 (1H, dd, J=5.0, 12.0 Hz), 3.79 (3H, s) 6.83 (2H, d, J=9.7 Hz), 7.09 (2H, d, J=9.7 Hz)

(R)-3-Chloro-1-[3-(4-methoxyphenyl)propyl]homopiperidine (R)-2-Hydroxymethyl-1-[3-(4-methoxyphenyl)propyl]piperidine (422 mg) was dissolved in 10 ml of dichloromethane. Triethylamine (210 mg, 2.08 mmol) and methanesulfonyl chloride (238 mg, 2.08 mmol) were added to the obtained solution under stirring under cooling on ice. They were stirred under cooling on ice for 1 hour and then at room temperature for 18 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-[3-(4-methoxyphenyl) propyl]homopiperidine in the form of a light yellow oil (278 mg, 62%).

NMR (CDCl$_3$) δ: 1.28–1.40 (2H, m), 1.50–1.82 (6H, m), 2.24–2.33 (1H, m), 2.43–2.60 (3H, m), 2.64–2.76 (2H, m), 2.78–2.85 (1H, m), 3.56 (1H, dd, J=4.0, 12.0 Hz), 3.59 (1H, dd, J=7.0, 12.0 Hz), 3.79 (3H, s), 6.81 (2H, d, J=9.7 Hz), 7.10 (2H, d, J=9.7 Hz)

(R)-5,11-Dihydro-5-[1-[3-(4-methoxyphenyl)propyl]piperidine-2-ylmethyl] dibenzo[b,e][1,4]oxazepine 60% Sodium hydride (39 mg, 0.99 mmol) was washed with hexane under argon atmosphere, and then suspended in dimethyl sulfoxide (6 ml). The obtained suspension was stirred at room temperature for 30 minutes. 5,11-Dihydrodibenzo[b,e][1,4]oxazepine (178 mg, 0.90 mmol) was added to the suspension, and they were stirred at room temperature for 20 minutes and then at 50° C. for 30 minutes. A solution of (R)-3-chloro-1-[3-(4-methoxyphenyl)propyl]homopiperidine (278 mg, 0.99 mmol) in dimethyl sulfoxide (3 ml) was added dropwise into the obtained solution, and they were stirred at 50° C. for 3 hours. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (10:1) and then with hexane and ethyl acetate (3:1). The appropriate fractions were combined, and the solvent was evaporated under reduced pressure to obtain (R)-5,11-dihydro-5-[1-[3-(4-methoxyphenyl) propyl]piperidine-2-ylmethyl]dibenzo[b,e][1,4]oxazepine in the form of a light yellow oil (196 mg, 49%).

NMR (CDCl$_3$) δ: 1.23–1.80 (8H, m), 2.16–2.25 (1H, m), 2.30–2.44 (1H, m), 2.51–2.94 (5H, m), 3.23–3.38 (1H, m), 3.78 (3H, s), 3.97–4.08 (1H, m), 5.12 (1H, d, J=13.0 Hz), 5.21 (1H, d, J=13.0 Hz), 6.65–6.83 (5H, m), 6.95–7.28 (7H, m)

(R)-5,11-Dihydro-5-[1-[3-(4-methoxyphenyl)propyl]piperidine-2-ylmethyl]dibenzo[b,e][1,4]oxazepine Hydrochloride 1.0 ml of 4 M hydrochloric acid/ethyl acetate was added to a solution of (R)-5,11-dihydro-5-[1-[3-(4-methoxyphenyl)propyl]piperidine-2-ylmethyl]dibenzo[b,e][1,4]oxazepine (196 mg) in dichloromethane (5 ml), and they were stirred for 2 hours. The solvent was evaporated under reduced pressure. The title compound was obtained in the form of a light yellow solid (180 mg, 85%).

ESI/Mass: 429 [M+H]$^+$

NMR (CD$_3$OD) δ: 1.70–2.22 (8H, m), 2.50–2.65 (1H, m), 2.88–3.22 (4H, m), 3.43–3.55 (1H, m) ,3.74 (3H, s), 3.98–4.08 (1H, m),4.13–4.32 (2H, m), 5.19 (1H, d, J=13.7 Hz), 5.25 (1H, d, J=13.7 Hz), 6.60–6.92 (5H, m), 7.00–7.38 (7H, m)

Example 5

(R)-5,11-Dihydro-5-[1-(3,4-methylenedioxyphenethyl) piperidine-2-yl-methyl] dibenzo[b,e][1,4]oxazepine Hydrochloride (R)-2-Hydroxymethyl-1-(3,4-methylenedioxyphenethyl)piperidine (R)-2-hydroxymethylpiperidine (288 mg, 2.50 mmol), 3,4-methylenedioxyphenethyl mesylate (732 mg, 3.00 mmol), sodium carbonate (320 mg, 3.00 mmol) and sodium iodide (30 mg, 0.20 mmol) were added to acetonitrile (25 ml), and they were heated under reflux at 90° C. for 10 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with dichloromethane as the eluent and then with dichloromethane and methanol (20:1). The appropriate fractions were combined, and the solvent was evaporated under reduced pressure to obtain (R)-2-hydroxymethyl-1-(3,4-methylenedioxyphenethyl)piperidine in the form of a light yellow oil (370 mg, 56%).

NMR (CDCl$_3$) δ: 1.49–1.72 (6H, m), 2.32–2.47 (3H, m), 2.60–2.72 (2H, m). 2.87–2.93 (1H, m), 3.01–3.08 (1H, m), 3.44 (1H, dd, J=4.7, 12.0 Hz), 3.72 (1H, dd, 4.7, 12.0 Hz), 5.91 (2H, s) 6.62 (1H, dd, J=2.0, 9.0 Hz), 6.67 (1H, d, J=2.0 Hz), 6.73 (1H, d, J=9.0)

(R)-3-Chloro-1-(3,4-methylenedioxyphenethyl)homopiperidine (R)-2-Hydroxymethyl-1-(3,4-methylenedioxyphenethyl)piperidine (370 mg) was dissolved in 10 ml of dichloromethane. Triethylamine (184 mg, 1.82 mmol) and methanesulfonyl chloride (208 mg, 1.82 mmol) were added to the obtained solution under stirring under cooling on ice. They were stirred under cooling on ice for 1 hour and then at room temperature for 14 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-(3,4-methylenedioxyphenethyl) homopiperidine in the form of a light yellow oil (375 mg, 95%).

NMR (CDCl$_3$) δ: 1.32–1.43 (2H, m), 1.60–1.73 (4H, m), 2.35–2.44 (1H, m), 2.62–2.78 (4H, m), 2.83–2.90 (2H, m), 3.61 (1H, dd, J=3.3, 12.7 Hz), 3.66 (1H, dd, J=7.0, 12.7 Hz), 5.92 (2H, s), 6.63 (2H, dd, J=2.0, 9.0 Hz), 6.69 (1H, d, J=9.0 Hz), 6.73 (1H, J=9.0 Hz)

(R)-5,11-Dihydro-5-[1-(3,4-methylenedioxyphenethyl) piperidine-2-yl-methyl]dibenzo[b,e][1,4]oxazepine 60% Sodium hydride (56 mg, 1.4 mmol) was washed with hexane under argon atmosphere, and then suspended in dimethyl sulfoxide (10 ml). The obtained suspension was stirred at room temperature for 30 minutes. 5,11-Dihydrodibenzo[b,e][1,4]oxazepine (250 mg, 1.27 mmol) was added to the suspension, and they were stirred at room temperature for 30 minutes and then at 50° C. for 30 minutes. A solution of (R)-3-chloro-1-(3,4-methylenedioxyphenethyl)homopiperidine (426 mg, 1.40 mmol) in dimethyl sulfoxide (5 ml) was added dropwise into the obtained solution, and they were stirred at 50° C. for 2 hours. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (10:1) and then with hexane and ethyl acetate (4:1). The appropriate fractions were combined, and the solvent was evaporated under reduced pressure to obtain (R)-5,11-dihydro-5-[1-(3,4-methylenedioxyphenethyl)piperidine-2-ylmethyl] dibenzo [b,e][1,4] oxazepine in the form of a light yellow oil (171 mg, 30%).

NMR (CDCl$_3$) δ: 1.40–1.80 (6H, m), 2.21–2.31 (1H, m), 2.52–2.75 (4H, m), 2.88–3.05 (2H, m), 3.66 (1H, dd, J=7.0, 15.0 Hz), 3.94 (1H, dd, J=5.0, 15.0 Hz), 5.11 (1H, d, J=13.3

Hz), 5.21 (1H, d, J=13.3 Hz), 5.92 (2H, s), 6.68–6.84 (3H, m), 6.91–7.09 (4H, m), 7.13–7.33 (4H, m)

(R)-5,11-Dihydro-5-[1-(3,4-methylenedioxyphenethyl) piperidine-2-yl-methyl]dibenzo[b,e][1,4]oxazepine Hydrochloride 1.5 ml of 4 M hydrochloric acid/ethyl acetate was added to a solution of (R)-5,11-dihydro-5-[1-(3,4-methylenedioxyphenethyl) piperidine-2-ylmethyl] dibenzo [b,e][1,4] oxazepine (171 mg) in dichloromethane (5 ml), and they were stirred for 2 hours. The solvent was evaporated under reduced pressure. The title compound was obtained in the form of a white solid (150 mg, 80%).

ESI/Mass: 429 [M+H$^+$]

NMR (CD$_3$OD) δ: 1.42–1.95 (5H, m), 2.14–2.25 (1H, m), 2.75–3.10 (3H, m), 3.20–3.40 (2H, m), 3.65–3.77 (2H, m), 4.05–4.30 (2H, m), 4.89 (1H, d, J=14.0 Hz), 5.01 (1H, d, J=14.0 Hz), 5.94 (2H, m), 6.60–6.93 (5H, m), 7.02–7.39 (6H, m)

Example 6

(R)-5-[1-(4-chlorophenethyl)piperidine-2-ylmethyl]-5,11-dihydrodibenzo [b,e][1,4]oxazepine Hydrochloride (R)-1-(4-Chlorophenethyl)-2-hydroxymethylpiperidine (R)-2-hydroxymethylpiperidine (288 mg, 2.50 mmol), 4-chlorophenethyl tosylate (931 mg, 3.00 mmol), sodium carbonate (320 mg, 3.00 mmol) and sodium iodide (30 mg, 0.20 mmol) were added to acetonitrile (25 ml), and they were heated under reflux at 90° C. for 10 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with dichloromethane and then with dichloromethane and methanol (20:1). The appropriate fractions were combined, and the solvent was evaporated under reduced pressure to obtain (R)-1-(4-chlorophenethyl)-2-hydroxymethylpiperidine in the form of a light yellow oil (354 mg, 56%).

NMR (CDCl$_3$) δ: 1.30–1.73 (6H, m), 2.32–2.47 (2H, m), 2.62–2.76 (3H, m), 2.89–3.07 (2H, m), 3.44 (1H, dd, J=4.7, 12.0 Hz), 3.71 (1H, dd, J=4.7, 12.0 Hz), 7.11 (2H, d, J=9.3 Hz), 7.24 (2H, d, J=9.3 Hz)

(R)-3-Chloro-1-(4-chlorophenethyl)homopiperidine (R)-1-(4-chlorophenethyl)-2-hydroxymethylpiperidine (354 mg) was dissolved in 10 ml of dichloromethane. Triethylamine (184 mg, 1.82 mmol) and methanesulfonyl chloride (208 mg, 1.82 mmol) were added to the obtained solution under stirring under cooling on ice. They were stirred under cooling on ice for 1 hour and then at room temperature for 14 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-(4-chlorophenethyl) homopiperidine in the form of a light yellow oil (380 mg, 100%).

NMR (CDCl$_3$) δ: 1.30–1.43 (1H, m), 1.54–1.74 (5H, m), 2.36–2.44 (1H, m), 2.60–2.78 (4H, m), 2.83–2.93 (2H, m), 3.58 (1H, dd, J=4.0, 12.7 Hz), 3.64 (1H, dd, J=7.0, 12.7 Hz), 7.12 (2H, d, J=9.0 Hz), 7.24 (2H, d, J=9.0 Hz)

(R)-5-[1-(4-chlorophenethyl)piperidine-2-ylmethyl]-5,11-dihydrodibenzo [b,e][1,4]oxazepine 60% Sodium hydride (56 mg, 1.4 mmol) was washed with hexane under argon atmosphere, and then suspended in dimethyl sulfoxide (10 ml). The obtained suspension was stirred at room temperature for 30 minutes. 5,11-Dihydrodibenzo[b,e][1,4]oxazepine (250 mg, 1.27 mmol) was added to the suspension, and they were stirred at room temperature for 30 minutes and then at 50° C. for 30 minutes. A solution of (R)-3-chloro-1-(4-chlorophenethyl) homopiperidine (380 mg, 1.40 mmol) in dimethyl sulfoxide (5 ml) was added dropwise into the obtained solution, and they were stirred at 50° C. for 2 hours. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (5:1) and then with hexane and ethyl acetate (2:1). The appropriate fractions were combined, and the solvent was evaporated under reduced pressure to obtain (R)-5-[1-(4-chlorophenethyl)piperidine-2-ylmethyl]-5,11-dihydro-dibenzo[b,e][1,4]oxazepine in the form of a light yellow solid (160 mg, 29%).

NMR (CDCl$_3$) δ: 1.35–1.60 (5H, m), 1.70–1.86 (1H, m), 2.22–2.31 (1H, m), 2.50–2.73 (4H, m), 2.90–3.02 (2H, m), 3.65 (1H, dd, J=7.0, 15.0 Hz), 3.93 (1H, dd, J=5.0, 15.0 Hz), 5.11 (1H, d, J=13.3 Hz), 5.19 (1H, d, J=13.3 Hz), 6.76–6.84 (3H, m), 6.91–7.06 (3H, m), 6.96 (2H, d, J=9.7 Hz), 7.17–7.32 (2H, m), 7.19 ((2H, d, J=9.7 Hz)

(R)-5-[1-(4-chlorophenethyl)piperidine-2-ylmethyl]-5,11-dihydrodibenzo [b,e][1,4]oxazepine Hydrochloride 1.5 ml of 4 M hydrochloric acid/ethyl acetate was added to a solution of (R)-5-[1-(4-chlorophenethyl)piperidine-2-ylmethyl]-5,11-dihydrodibenzo[b,e][1,4]oxazepine (160 mg) in dichloromethane (5 ml), and they were stirred for 2 hours. The solvent was evaporated under reduced pressure. The title compound was obtained in the form of a white solid (155 mg, 87%).

ESI/Mass: 429 [M+H$^+$]

NMR (CD$_3$OD) δ: 1.75–2.00 (5H, m), 2.20–2.28 (1H, m), 2.83–3.12 (3H, m), 3.28–3.40 (2H, m), 3.68–3.80 (2H, m), 4.10–4.30 (2H, m), 4.89 (1H, d, J=14.0 Hz), 4.98 (1H, d, J=14.0 Hz), 6.78–6.04 (3H, m), 7.02–7.12 (3H, m), 7.16–7.41 (6H, m)

Example 7

(R)-5,11-Dihydro-5-[1-(4-dimethylaminophenethyl) piperidine-2-ylmethyl]dibenzo[b,e][1,4]oxazepine Dihydrochloride (R)-2-Hydroxymethyl-1-(4-dimethylaminophenethyl) piperidine (R)-2-hydroxymethylpiperidine (288 mg, 2.50 mmol), 4-dimethylaminophenethyl mesylate (729 mg, 3.00 mmol), sodium carbonate (320 mg, 3.00 mmol) and sodium iodide (30 mg, 0.20 mmol) were added to acetonitrile (25 ml), and they were heated under reflux at 90° C. for 8 hours. The solvent was evaporated under reduced pressure. The residue was distributed in ethyl acetate and saturated aqueous sodium hydrogencarbonate solution. The organic layer was washed with water and dried over magnesium sulfate. Then the solvent was evaporated under reduced pressure. The obtained residue was subjected to silica gel column chromatography. The product was eluted with dichloromethane and then with dichloromethane and methanol (20:1). The appropriate fractions were combined, and the solvent was evaporated under reduced pressure to obtain (R)-2-hydroxymethyl-1-(4-dimethyl-aminophenethyl)piperidine in the form of a light yellow oil (452 mg, 69%).

NMR (CDCl$_3$) δ: 1.30–1.73 (6H, m), 2.38–2.54 (2H, m), 2.68–2.75 (4H, m). 2.90 (6H, s), 3.08–3.16 (1H, m), 3.47 (1H, dd, J=4.7, 12.0 Hz), 3.76 (1H, dd, J=4.7, 12.0 Hz), 6.68 (2H, d, J=10.0 Hz), 7.06 (2H, d, J=10.0 Hz)

(R)-3-Chloro-1-(4-dimethylaminophenethyl) homopiperidine (R)-2-Hydroxymethyl-1-(4-dimethylaminophenethyl) piperidine (452 mg, 1.72 mmol) was dissolved in 10 ml of dichloromethane. Triethylamine (226 mg, 2.26 mmol) and methanesulfonyl chloride (260 mg, 2.26 mmol) were added to the obtained solution under stirring under cooling on ice. They were stirred under cooling on ice for 1 hour and then at room temperature for 14 hours. The reaction liquid was distributed in dichloromethane and saturated aqueous sodium hydrogencarbonate solution. The organic layer was dried over magnesium sulfate, and the solvent was evaporated under reduced pressure to obtain (R)-3-chloro-1-(4-dimethylaminophenethyl) homo-piperidine in the form of a light yellow oil (470 mg, 97%).

NMR (CDCl$_3$) δ: 1.30–1.45 (1H, m), 1.53–1.73 (5H, m), 2.38–2.48 (1H, m), 2.60–2.75 (4H, m), 2.82–2.92 (2H, m), 2.91 (6H, s), 3.61 (1H, dd, J=3.3, 12.3 Hz), 3.68 (1H, dd, J=6.7, 12.3 Hz), 6.70 (2H, d, J=9.7 Hz), 7.06 (2H, d, J=9.7 Hz)

(R)-5,11-Dihydro-5-[1-(4-dimethylaminophenethyl) piperidine-2-ylmethyl]dibenzo[b,e][1,4]oxazepine 60% Sodium hydride (67 mg, 1.68 mmol) was washed with hexane under argon atmosphere, and then suspended in dimethyl sulfoxide (10 ml). The obtained suspension was stirred at room temperature for 30 minutes. 5,11-Dihydrodibenzo[b,e][1,4]oxazepine (300 mg, 1.53 mmol) was added to the suspension, and they were stirred at room temperature for 30 minutes and then at 50° C. for 30 minutes. A solution of (R)-3-chloro-1-(4-dimethylaminophenethyl)homopiperidine (470 mg, 1.68 mmol) in dimethyl sulfoxide (5 ml) was added dropwise into the obtained solution, and they were stirred at 50° C. for 3 hours. The reaction liquid was distributed in saturated aqueous sodium hydrogencarbonate solution and ethyl acetate. The organic layer was dried, and the solvent was evaporated under reduce pressure. The obtained residue was subjected to silica gel column chromatography. The product was eluted with hexane and ethyl acetate (10:1), then with hexane and ethyl acetate (4:1) and finally with hexane and ethyl acetate (1:1). The appropriate fractions were combined, and the solvent was evaporated under reduced pressure to obtain (R)-5,11-dihydro-5-[1-(4-dimethylaminophenethyl) piperidine-2-ylmethyl] dibenzo[b,e][1,4]oxazepine in the form of a light yellow solid (224 mg, 33%).

NMR (CDCl$_3$) δ: 1.30–1.60 (5H, m), 1.75–1.84 (1H, m), 2.29–2.37 (1H, m), 2.57–2.72 (5H, m), 2.92 (6H, s), 2.95–3.04 (1H, m), 3.63 (1H, dd, J=8.3, 15.0 Hz), 4.10 (1H, dd, J=5.3, 15.0 Hz), 5.15 (1H, d, J=13.3 Hz), 5.23 (1H, d, J=13.3 Hz), 6.68 (2H, d, J=9.7 Hz), 6.72–6.84 (3H, m), 6.97 (2H, d, J=9.7 Hz), 6.99–7.11 (2H, m), 7.22–7.33 (3H, m)

(R)-5,11-dihydro-5-[1-(4-dimethylaminophenethyl) piperidine-2-ylmethyl]dibenzo[b,e][1,4]oxazepine Dihydrochloride 1.5 ml of 4 M hydrochloric acid/ethyl acetate was added to a solution of (R)-5,11-dihydro-5-[1-(4-dimethylaminophenethyl)piperidine-2-ylmethyl]dibenzo[b,e][1,4]oxazepine (171 mg) in dichloromethane (5 ml), and they were stirred for 2 hours. The solvent was evaporated under reduced pressure. The title compound was obtained in the form of a light yellow solid (220 mg, 84%).

ESI/Mass: 429 [M+H$^+$]

NMR (CD$_3$OD) δ: 1.82–2.02 (5H, m), 2.20–2.28 (1H, m), 2.96–3.11 (2H, m), 3.15–3.41 (3H, m), 3.30 (6H, s), 3.71–3.81 (2H, m), 4.14–4.37 (2H, m), 4.92 (1H, d, J=14.0 Hz), 4.97 (1H, d, J=14.0 Hz), 6.76–6.95 (3H, m), 7.07–7.12 (2H, m), 7.23 (2H, d, J=9.0 Hz), 7.28–7.49 (3H, m), 7.58 (2H, d, J=9.0 Hz)

Example 8

(R)-5,11-Dihydro-5-[1-(4-methoxyphenethyl) pyrrolidine-3-yl] dibenzo[b,e][1,4]oxazepine Hydrochloride (S)-3-(4-Nitrobenzoyloxy)pyrrolidine 4 M hydrochloric acid/dioxane (3.0 ml) was added to a solution of (S)-1-t-butoxycarbonyl-3-(4-nitrobenzoyloxy) pyrrolidine [J. Org. Chem. 59, 2289 (1994)] (1.68 g, 5 mmol) in dioxane (10 ml), and they were stirred for 2 hours. The reaction liquid was poured into 1 M-aqueous NaOH solution cooled on ice/water. After the extraction with ethyl acetate, the organic layer was dried and the solvent was evaporated under reduced pressure to obtain (S)-3-(4-nitrobenzoyloxy)pyrrolidine in the form of a light yellow oil (799 mg, 68%).

NMR (CDCl$_3$) δ: 1.97–2.08 (1H, m), 2.15–2.27 (1H, m), 2.97–3.05 (1H, m), 3.16–3.26 (3H, m), 5.49–5.54 (1H, m), 8.20 (2H, d, J=10.0 Hz), 8.28 (2H, d, J=10.0 Hz)

(S)-3-(4-Nitrobenzoyloxy)-1-(4-methoxyphenethyl) pyrrolidine

4-Methoxyphenethyl tosylate (1.24 g, 4.05 mmol), sodium carbonate (430 mg, 4.06 mmol) and sodium iodide (40 mg, 0.26 mmol) were added to a solution of (S)-3-(4-nitrobenzoyloxy)pyrrolidine (799 mg, 3.38 mmol) in acetonitrile (40 ml), and they were heated under reflux at 90° C. for 3 hours. The insoluble material was removed by the filtration. The insoluble material was washed with ethyl acetate, and the wash solution was combined with the filtrate. The solvent was evaporated under reduced pressure. The obtained residue was subjected to silica gel column chromatography. The product was eluted with hexane and ethyl acetate (10:1) and then with a mixture of the same solvents (1:1). The appropriate fractions were combined, and the solvent was evaporated under reduced pressure to obtain (S)-3-(4-nitrobenzoyloxy)-1-(4-methoxy-phenethyl) pyrrolidine in the form of a light yellow oil (1.00 g, 80%).

NMR (CDCl$_3$) δ: 1.99–2.10 (1H, m), 2.35–2.56 (2H, m), 2.63–2.82 (4H, m), 2.88–2.99 (3H, m), 3.79 (3H, s), 5.43–5.50 (1H, m), 6.83 (2H, d, J=10.0 Hz), 7.13 (2H, d, J=10.0 Hz), 8.22 (2H, d, J=10.0 Hz), 8.28 (2H, d, J=10.0 Hz)

(S)-3-Hydroxy-1-(4-methoxyphenethyl)pyrrolidine (S)-3-(4-Nitrobenzoyloxy)-1-(4-methoxyphenethyl) pyrrolidine (1.00 g, 2.70 mmol) was dissolved in methanol (20 ml), tetrahydrofuran (20 ml) and water (10 ml). 4 M-LiOH (3 ml) was added dropwise in the obtained solution, and they were stirred at room temperature for 1 hour. The solvent was evaporated under reduced pressure, and then the residue was distributed in water and ether. The organic layer was dried, and the solvent was evaporated under reduced pressure to obtain (S)-3-hydroxy-1-(4-methoxyphenethyl)pyrrolidine in the form of a light yellow oil (541 mg, 91%).

NMR (CDCl$_3$) δ: 1.64–1.80 (1H, m), 2.12–2.25 (2H, m), 2.51–2.56 (1H, m), 2.64–2.70 (2H, m), 2.73–2.78 (3H, m), 2.90–3.00 (1H, m), 3.79 (3H, s), 4.32–4.38 (1H, m), 6.83 (2H, d, J=9.7 Hz), 7.12 (2H, d, J=9.7 Hz)

(S)-3-Methanesulfonyloxy-1-(4-methoxyphenethyl) pyrrolidine (S)-3-Hydroxy-1-(4-methoxyphenethyl)pyrrolidine (541 mg, 2.45 mmol) was dissolved in dichloromethane (15 ml). Triethylamine (272 mg, 2.69 mmol) and methanesulfonyl chloride (295 mg, 2.58 mmol) were added to the obtained solution under stirring under cooling on ice. They were stirred at 0° C. for 1 hour. The reaction liquid was distributed in dichloromethane and water. The organic layer was dried, and the solvent was evaporated under reduce pressure. The obtained residue was subjected to silica gel column chromatography. The product was eluted with dichloromethane and then with a solvent mixture of dichloromethane and methanol (50:1). The appropriate fractions were combined, and the solvent was evaporated under reduced pressure to obtain (S)-3-methanesulfonyloxy-1-(4-methoxyphenethyl) pyrrolidine in the form of a white solid (734 mg, 100%).

Melting point: 70–71° C.

NMR (CDCl$_3$) δ: 2.05–2.15 (1H, m), 2.26–2.38 (1H, m), 2.45–2.53 (1H, m), 2.65–2.78 (4H, m), 2.79–2.99 (3H, m), 3.01 (3H, s), 3.79 (3H, s), 5.19–5.25 (1H, m), 6.82 (2H, d, J=10.0 Hz), 7.12 (2H, d, J=10.0 Hz), (R)-5,11-Dihydro-5-[1-(4-methoxyphenethyl)pyrrolidine-3-yl]dibenzo[b,e][1,4]oxazepine 60% sodium hydride (240 mg, 6.0 mmol) was washed with hexane under argon atmosphere, and then suspended in dimethyl sulfoxide (20 ml). After stirring at room temperature for 50 minutes, 5,11-dihydrodibenzo[b,e][1,4] oxazepine (1.20 g, 6.0 mmol) was added to the obtained suspension. They were stirred at room temperature for 60 minutes and then at 50° C. for 60 minutes. A solution of (S)-3-methanesulfonyloxy-1-(4-methoxyphenethyl) pyrrolidine (734 mg, 2.45 mmol) in dimethyl sulfoxide (10 ml) was added dropwise in the obtained solution, and they were stirred at 50° C. for 3 hours. The reaction liquid was poured into ice/water. After the extraction with a solvent mixture of hexane and ethyl acetate (1:1), the organic layer was dried and the solvent was evaporated under reduced pressure. The obtained residue was subjected to silica gel column chromatography. The product was eluted with hexane and ethyl acetate (10:1), then with a mixture of the same solvents (3:1) and finally with a mixture of them (2:1). The appropriate fractions were combined, and the solvent was evaporated under reduced pressure to obtain (R)-5,11-dihydro-5-[1-(4-methoxyphenethyl) pyrrolidine-3-yl]dibenzo[b,e][1,4]oxazepine in the form of a light yellow oil (0.36 g, 36%).

NMR (CDCl$_3$) δ: 1.74–1.83 (1H, m), 2.22–2.31 (1H, m), 2.39–2.43 (1H, m), 2.49–2.61 (2H, m), 2.63–2.76 (3H, m), 2.78–2.85 (1H, m), 3.19–3.24 (1H, m), 3.78 (3H, s), 4.67–4.74 (1H, m), 5.30–5.50 (2H, b), 6.72–6.84 (3H, m), 6.80 (2H, d, J=8.7 Hz), 6.94–6.96 (1H, m), 7.04–7.12 (2H, m), 7.08 (2H, d, J=8.7 Hz), 7.27–7.33 (2H, m)

(R)-5,11-Dihydro-5-[1-(4-methoxyphenethyl)pyrrolidine-3-yl]dibenzo[b,e][1,4]oxazepine Hydrochloride 2.0 ml of 4 M hydrochloric acid/dioxane was added to a solution of (R)-5,11-dihydro-5-[1-(4-methoxyphenethyl) pyrrolidine-3-yl]dibenzo[b,e][1,4]oxazepine (360 mg, 0.9 mmol) in dichloromethane (10 ml), and they were stirred for 1 hour. The solvent was evaporated under reduced pressure. The obtained residue was crystallized from ethanol to obtain the title compound in the form of a white solid (302 mg, 77%).

Melting point: 224–226° C.

ESI/Mass: 401 [M+H$^+$]

NMR (CD$_3$OD) δ: 1.90–2.10 (1H, b), 2.45–2.65 (1H, b), 2.93 (2H, t, J=6.7 Hz), 3.20–3.80 (3H, b), 3.42 (2H, t, J=6.7 Hz), 3.76 (3H, s), 5.06 (2H, s), 5.80–6.20 (2H, b), 6.72–6.75 (1H, m), 6.79–6.91 (4H, m), 6.97–7.00 (1H, m), 7.12–7.20 (4H, m), 7.36–7.42 (2H, m)

Example 9

(S)-5,11-Dihydro-5-[1-(4-methoxyphenethyl) pyrrolidine-3-yl]dibenzo[b,e][1,4]oxazepine Hydrochloride The title compound was obtained in the same manner as that of Example 8 except that (S)-3-hydroxy-1-(4-methoxyphenethyl)pyrrolidine was replaced with (R)-3-hydroxy-1-(4-methoxyphenethyl)pyrrolidine. ESI-MS and NMR spectra of this compound were the same as those of the compound of Example 8.

Melting point: 225–227° C.

Example 10

(R)-5,11-Dihydro-5-[1-(4-dimethylaminophenethyl) pyrrolidine-3-yl]dibenzo[b,e][1,4]oxazepine Hydrochloride (R)-1-(4-dimethylaminophenethyl)-3-hydroxypyrrolidine 4-Dimethylaminophenethyl tosylate (1.91 g, 6.0 mmol), sodium carbonate (750 mg, 7.0 mmol) and sodium iodide (40 mg, 0.26 mmol) were added to a solution of (R)-3-hydroxypyrrolidine (522 mg, 6.0 mmol) in acetonitrile (40 ml), and they were heated under reflux at 90° C. for 4 hours. The solvent was evaporated under reduced pressure. The obtained residue was distributed in 2 M NaOH and chloroform. The organic layer was dried and the solvent was evaporated under reduced pressure. The residue was subjected to silica gel column chromatography. The product was eluted with dichloromethane, then with dichloromethane and methanol (50:1) and finally with a mixture of the same solvents (20:1). The appropriate fractions were combined, and the solvent was evaporated under reduced pressure to obtain (R)-1-(4-dimethylaminophenethyl)-3-hydroxypyrrolidine in the form of a light yellow oil (1.00 g, 71%).

NMR (CDCl$_3$) δ: 1.65–1.80 (1H, m), 2.15–2.35 (2H, m), 2.50–2.56 (1H, m), 2.64–2.78 (5H, m), 3.79 (6H, s), 2.92–3.00 (1H, m), 4.29–4.36 (1H, m), 6.69 (2H, d, J=9.7 Hz), 7.08 (2H, d, J=9.7 Hz)

(S)-1-(4-Dimethylaminophenethyl)-3-(4-nitrobenzoyloxy) pyrrolidine

Triphenylphosphine (1.72 g, 5.13 mmol) and 4-nitrobenzoic acid (0.86 g, 5.13 mmol) were added to a solution of (R)-1-(4-dimethylaminophenethyl)-3-hydroxypyrrolidine in anhydrous tetrahydrofuran (20 ml) under argon atmosphere. 40% solution (2.32 ml, 5.13 mmol) of diethyl azodicarboxylate in toluene was added dropwise in the obtained mixture under stirring at room temperature. After stirring at room temperature for 2 hours, 60 ml of ether was added to the reaction liquid. The reaction mixture was washed with water, then with saturated aqueous sodium hydrogencarbonate solution and finally with saturated aqueous sodium chloride solution. The organic layer was dried, and the solvent was evaporated under reduced pressure. Ethyl acetate and hexane were added to the obtained residue, and the crystals thus formed were taken by the filtration. The filtrate was evaporated under reduced pressure, and the residue was distributed in dichloromethane and 1 M-HCl. 4M-NaOH was added to the aqueous layer to make it strongly alkaline. After the extraction with dichloromethane, the organic layer was dried and the solvent was distilled under reduced pressure. The residue was subjected to silica gel column chromatography. The product was eluted with hexane and ethyl acetate (10:1), then with a mixture of the same solvents (3:1) and finally with a mixture of the same solvents (1:1). The appropriate fractions were combined, and the solvent was evaporated under reduced pressure to obtain the title compound in the form of a light yellow oil (860 mg, 64%).

NMR (CDCl$_3$) δ: 1.99–2.10 (1H, m),2.35–2.56 (2H, m),2.63–2.82 (4H, m), 3.79 (3H, s), 2.88–2.99 (3H, m), 5.43–5.50 (1H, m), 6.69 (2H, d, J=10.0 Hz), 7.09 (2H, d, J=10.0 Hz), 8.22 (2H, d, J=10.0 Hz), 8.28 (2H, d, J=10.0 Hz)

(S)-1-(4-Dimethylaminophenethyl)-3-hydroxypyrrolidine (S)-1-(4-dimethylaminophenethyl)-3-(4-nitrobenzoyloxy) pyrrolidine (1.00 g, 2.70 mmol) was dissolved in methanol (20 ml), tetrahydrofuran (20 ml) and water (10 ml). 4M-LiOH (3 ml) was added dropwise in the obtained solution, and they were stirred at room temperature for 1 hour. The solvent was evaporated under reduced pressure, and the residue was distributed in water and ether. The organic layer was dried and the solvent was evaporated under reduced pressure to obtain (S)-1-(4-dimethylaminophenethyl)-3-hydroxypyrrolidine in the form of a light yellow solid (320 mg, 62%).

NMR (CDCl$_3$) δ: 1.65–1.80 (1H, m), 2.15–2.35 (2H, m), 2.50–2.56 (1H, m), 2.64–2.78 (5H, m), 3.79 (6H, s), 2.92–3.00 (1H, m), 4.29–4.36 (1H, m), 6.69 (2H, d, J=9.7 Hz), 7.08 (2H, d, J=9.7 Hz)

(S)-1-(4-Dimethylaminophenethyl)-3-methanesulfonyloxypyrrolidine (S)-1-(4-dimethylaminophenethyl)-3-hydroxypyrrolidine (320 mg, 1.37 mmol) was dissolved in dichloromethane (10 ml). Triethylamine (152 mg, 1.50 mmol) and methanesulfonyl chloride (164 mg, 1.43 mmol) were added to the obtained solution under stirring under cooling on ice. They were stirred at 0° C. for 1 hour. The reaction liquid was distributed in dichloromethane and water. The organic layer was dried, and the solvent was evaporated under reduce pressure. The obtained residue was subjected to silica gel column chromatography. The product was eluted with dichloromethane and then with a solvent mixture (50:1) of dichloromethane and methanol. The appropriate fractions were combined, and the solvent was evaporated under reduced pressure to obtain (S)-1-(4-dimethylaminophenethyl)-3-methanesulfonyloxy-pyrrolidine in the form of a light yellow oil (378 mg, 88%).

NMR (CDCl₃) δ: 2.04–2.15 (1H, m), 2.26–2.36 (1H, m), 2.45–2.52 (1H, m), 2.63–2.74 (4H, m), 2.82–2.98 (3H, m), 2.91 (6H, s), 3.02 (3H, s), 5.18–5.24 (1H, m), 6.69 (2H, d, J=9.7 Hz), 7.08 (2H, d, J=9.7 Hz), (R)-5,11-Dihydro-5-[1-(4-dimethylaminophenethyl)pyrrolidine-3-yl]dibenzo[b,e][1,4]oxazepine 60% sodium hydride (160 mg, 4.0 mmol) was washed with hexane under argon atmosphere, and then suspended in dimethyl sulfoxide (12 ml). After stirring at room temperature for 30 minutes, 5,11-dihydrodibenzo[b,e][1,4]oxazepine (790 g, 4.0 mmol) was added to the obtained suspension. They were stirred at room temperature for 60 minutes and then at 50° C. for 60 minutes. A solution of (S)-1-(4-dimethylaminophenethyl)-3-methanesulfonyloxypyrrolidine (378 mg, 1.21 mmol) in dimethyl sulfoxide (7 ml) was added dropwise in the obtained solution, and they were stirred at 50° C. for 3 hours. The reaction liquid was poured into ice/water. After the extraction with ethyl acetate, the organic layer was dried and the solvent was evaporated under reduced pressure. The obtained residue was subjected to silica gel column chromatography. The product was eluted with hexane and ethyl acetate (10:1), then with hexane and ethyl acetate (3:1) and finally with a mixture of the same solvents (1:1). The appropriate fractions were combined, and the solvent was evaporated under reduced pressure to obtain (R)-5,11-dihydro-5-[1-(4-dimethylaminophenethyl)pyrrolidine-3-yl]dibenzo[b,e][1,4]oxazepine in the form of a light yellow oil (196 mg, 39%).

NMR (CDCl₃) δ: 1.74–1.84 (1H, m), 2.22–2.34 (1H, m), 2.37–2.43 (1H, m), 2.48–2.72 (5H, m), 2.80–2.87 (1H, m), 2.90 (6H, s), 3.21–3.27 (1H, m), 4.67–4.76 (1H, m), 5.30–5.53 (2H, m), 6.68 (2H, d, J=9.7 Hz), 6.72–6.85 (3H, m), 6.95–6.98 (1H, m), 7.04 (2H, d, J=9.7 Hz), 7.05–7.14 (2H, m), 7.28–7.34 (2H, m)

(R)-5,11-Dihydro-5-[1-[(4-dimethylaminophenyl)ethyl]pyrrolidine-3-yl]dibenzo[b,e][1,4]oxazepine Dihydrochloride 1.0 ml of 4 M hydrochloric acid/ethyl acetate was added to a solution of (R)-5,11-dihydro-5-[1-(4-dimethylaminophenethyl)pyrrolidine-3-yl]dibenzo[b,e][1,4]oxazepine (196 mg) in dichloromethane (5 ml), and they were stirred for 1 hour. The solvent was evaporated under reduced pressure to obtain the title compound in the form of a light yellow solid (205 mg, 89%).

Melting point: 219–220° C.

ESI/Mass: 414 [M+H⁺]

NMR (CD₃OD) δ: 1.90–2.25 (1H, b), 2.40–2.73 (1H, b), 3.03–3.18 (2H, m), 3.24–3.42 (2H, m), 3.28 (6H, s), 3.45–3.54 (2H, m), 3.70–3.83 (1H, m), 4.08–4.12 ((1H, m), 5.02–5.17 (1H, m), 5.80–6.30 (2H, b), 6.71–7.06 (4H, m), 7.15–7.24 (2H, m), 7.36–7.43 (2H, m), 7.48–7.54 (2H, m), 7.61–7.64 (2H, m)

Example 11

(R)-5,11-Dihydro-5-[1-[3-(4-methoxyphenyl)propyl]pyrrolidine-3-yl]dibenzo[b,e][1,4]oxazepine Hydrochloride (S)-3-(4-Nitrobenzoyloxy)-1-[3-(4-methoxyphenyl)propyl]pyrrolidine 3-(4-Methoxyphenyl)propyl mesylate (732 mg, 3.00 mmol), sodium carbonate (320 mg, 3.00 mmol) and sodium iodide (30 mg, 0.20 mmol) were added to a solution of (S)-3-(4-nitrobenzoyloxy)pyrrolidine (472 mg, 2.00 mmol) in acetonitrile (25 ml), and they were heated under reflux at 90° C. for 6 hours. The solvent was evaporated under reduced pressure. The obtained residue was subjected to silica gel column chromatography. The product was eluted with hexane and ethyl acetate (10:1) and then with a mixture of the same solvents (1:1). The appropriate fractions were combined, and the solvent was evaporated under reduced pressure to obtain (S)-3-(4-nitrobenzoyloxy)-1-[3-(4-methoxyphenyl)propyl]pyrrolidine in the form of a light yellow oil (507 mg, 66%).

NMR (CDCl₃) δ: 1.82 (2H, q, J=8.7 Hz), 1.96–2.07 (1H, m), 2.23–2.55 (4H, m), 2.61 (2H, t, J=8.7 Hz), 2.85–2.90 (3H, m), 3.79 (3H, s), 4.90–4.97 (1H, m), 6.83 (2H, d, J=9.3 Hz), 7.10 (2H, d, J=9.3 Hz), 8.21 (2H, d, J=9.7 Hz), 8.27 (2H, d, J=9.3 Hz)

(S)-3-Hydroxy-1-[3-(4-methoxyphenyl)propyl]pyrrolidine (S)-3-(4-Nitrobenzoyloxy)-1-[3-(4-methoxyphenyl)propyl]pyrrolidine (507 mg, 1.32 mmol) was dissolved in methanol (10 ml). 1 M-NaOH (1.5 ml) was added dropwise in the obtained mixture. After stirring at room temperature for 1 hour, the solvent was evaporated under reduced pressure. The residue was distributed in water and ethyl acetate. The organic layer was dried, and the solvent was evaporated under reduced pressure to obtain (S)-3-hydroxy-1-[3-(4-methoxyphenyl)propyl] pyrrolidine in the form of a light yellow oil (310 mg, 100%).

NMR (CDCl₃) δ: 1.78–1.91 (3H, m), 2.15–2.26 (1H, m), 2.32–2.40 (1H, m), 2.52–2.64 (5H, m), 2.83–2.86 (1H, m), 2.99–3.07 (1H, m), 3.79 (3H, s), 4.44–4.50 (1H, m), 6.83 (2H, d, J=9.7 Hz), 7.10 (2H, d, J=9.7 Hz)

(S)-3-Methanesulfonyloxy-1-[3-(4-methoxyphenyl)propyl]pyrrolidine (S)-3-Hydroxy-1-[3-(4-methoxyphenyl)propyl]pyrrolidine (310 mg, 1.32 mmol) was dissolved in dichloromethane (10 ml). Triethylamine (173 mg, 1.71 mmol) and methanesulfonyl chloride (196 mg, 1.71 mmol) were added to the obtained solution under stirring under cooling on ice. They were stirred at 0° C. for 1 hour. The reaction liquid was distributed in dichloromethane and water. The organic layer was dried, and the solvent was evaporated under reduce pressure. The obtained residue was subjected to silica gel column chromatography. The product was eluted with dichloromethane and then with a solvent mixture (50:1) of dichloromethane and methanol. The appropriate fractions were combined, and the solvent was evaporated under reduced pressure to obtain (S)-3-methanesulfonyloxy-1-[3-(4-methoxyphenyl)propyl] pyrrolidine in the form of a light yellow oil (336 mg, 81%).

NMR (CDCl₃) δ: 1.79 (2H, q, J=8.3 Hz), 2.02–2.12 (1H, m), 2.24–2.33 (1H, m), 2.38–2.50 (3H, m), 2.59 (2H, t, J=8.3 Hz), 2.75–2.91 (3H, m), 3.01 (3H, s), 3.79 (3H, s), 5.17–5.24 (1H, m), 6.83 (2H, d, J=9.7 Hz), 7.10 (2H, d, J=9.7 Hz)

(R)-5,11-Dihydro-5-[1-[3-(4-methoxyphenyl)propyl]pyrrolidine-3-yl]dibenzo[b,e][1,4]oxazepine 60% sodium hydride (32 mg, 0.81 mmol) was washed with hexane under argon atmosphere, and then suspended in dimethyl sulfoxide (6 ml). After stirring at room temperature for 30 minutes, 5,11-dihydrodibenzo[b,e][1,4]oxazepine (142 g, 0.74 mmol) was added to the obtained suspension.

They were stirred at room temperature for 40 minutes and then at 50° C. for 40 minutes. A solution of (S)-3-methanesulfonyloxy-1-[3-(4-methoxyphenyl)propyl]pyrrolidine (254 mg, 1.81 mmol) in dimethyl sulfoxide (3 ml) was added dropwise in the obtained solution, and they were stirred at 50° C. for 5 hours. The reaction liquid was poured into ice/water. After the extraction with a solvent mixture of hexane and ethyl acetate (1:1), the organic layer was dried and the solvent was evaporated under reduced pressure. The obtained residue was subjected to silica gel column chromatography. The product was eluted with dichloromethane and then with a mixture of dichloromethane and methanol (50:1). The appropriate fractions were combined, and the solvent was evaporated under reduced pressure to obtain (R)-5,11-dihydro-5-[1-[3-(4-methoxyphenyl)propyl]pyrrolidine-3-yl]dibenzo[b,e][1,4]oxazepine in the form of a light yellow oil (78 mg, 25%).

NMR (CDCl$_3$) δ: 1.74–1.83 (3H, m), 2.22–2.31 (1H, m), 2.39–2.43 (1H, m), 2.49–2.61 (2H, m), 2.63–2.76 (3H, m), 2.78–2.85 (1H, m), 3.19–3.24 (1H, m), 3.78 (3H, s), 4.67–4.74 (1H, m), 5.30–5.50 (2H, b), 6.72–6.84 (3H, m), 6.80 (2H, d, J=8.7 Hz), 6.94–6.96 (1H, m), 7.04–7.12 (2H, m), 7.08 (2H, d, J=8.7 Hz), 7.27–7.33 (2H, m)

(R)-5,11-Dihydro-5-[1-[3-(4-methoxyphenyl)propyl]pyrrolidine-3-yl]dibenzo[b,e][1,4]oxazepine Hydrochloride 3.0 ml of 2 M hydrochloric acid/ethyl ether was added to a solution of (R)-5,11-dihydro-5-[1-[3-(4-methoxyphenyl)propyl]pyrrolidine-3-yl]dibenzo[b,e][1,4]oxazepine (78 mg, 0.19 mmol) in dichloromethane, and they were stirred for 1 hour. The solvent was evaporated under reduced pressure to obtain the title compound in the form of a light yellow solid (73 mg, 86%).

ESI/Mass: 401 [M+H$^+$]

NMR (CD$_3$OD) δ: 1.96 (3H, b), 2.19 (1H, b), 2.34 (1H, b), 2.60 (1H, b), 3.09–3.25 (3H, m), 3.49–3.58, 1H, m), 3.63–3.71 (2H, m), 3.74 (3H, s), 3.98–4.07 (1H, m), 5.00 (1H, b), 5.09 (1H, b), 6.69–6.75 (1H, m), 6.79–6.91 (4H, m), 6.97–7.00 (1H, m), 7.12–7.20 (4H, m), 7.35–7.40 (2H, m)

Example 12

(R)-5,11-Dihydro-5-[1-(3,4-methylenedioxyphenethyl)pyrrolidine-3-yl]dibenzo[b,e][1,4]oxazepine Hydrochloride (S)-3-(4-Nitrobenzoyloxy)-1-(3,4-methylenedioxyphenethyl)pyrrolidine 3,4-Methylenedioxyphenethyl mesylate (568 mg, 2.30 mmol), sodium carbonate (245 mg, 2.30 mmol) and sodium iodide (20 mg, 0.13 mmol) were added to a solution of (S)-3-(4-nitrobenzoyloxy)pyrrolidine (472 mg, 2.00 mmol) in acetonitrile (10 ml), and they were heated under reflux at 90° C. for 8 hours. The solvent was evaporated under reduced pressure. The obtained residue was subjected to silica gel column chromatography. The product was eluted with hexane and ethyl acetate (10:1) and then with a mixture of the same solvents (1:1). The appropriate fractions were combined, and the solvent was evaporated under reduced pressure to obtain (S)-3-(4-nitrobenzoyloxy)-1-(3,4-methylene-dioxyphenethyl)pyrrolidine in the form of a light yellow oil (474 mg, 62%).

NMR (CDCl$_3$) δ: 1.98–2.09 (1H, m), 2.35–2.55 (2H, m), 2.63–2.79 (4H, m), 2.86–2.98 (3H, m), 5.43–5.49 (1H, m), 5.92 (2H, s), 6.64–6.74 (3H, m), 8.22 (2H, d, J=9.7 Hz), 8.28 (2H, d, J=9.7 Hz)

(S)-3-Hydroxy-1-(3,4-methylenedioxyphenethyl)pyrrolidine (S)-3-(4-Nitrobenzoyloxy)-1-(3,4-methylenedioxyphenethyl) pyrrolidine (474 mg, 1.23 mmol) was dissolved in methanol (10 ml). 1 M-NaOH (1.5 ml) was added dropwise in the obtained mixture. After stirring at room temperature for 1 hour, the solvent was evaporated under reduced pressure. The residue was distributed in water and ethyl acetate. The organic layer was dried, and the solvent was evaporated under reduced pressure to obtain (S)-3-hydroxy-1-(3,4-methylenedioxyphenethyl) pyrrolidine in the form of a light yellow solid (281 mg, 97%).

NMR (CDCl$_3$) δ: 1.75–1.85 (1H, m), 2.16–2.27 (1H, m), 2.36–2.44 (1H, m), 2.58–2.63 (1H, m), 2.72–2.86 (5H, m), 2.99–3.06 (1H, m), 4.32–4.38 (1H, m), 5.92 (2H, s), 6.64–6.74 (3H, m)

(S)-3-Methanesulfonyloxy-1-(3,4-methylenedioxyphenethyl)pyrrolidine (S)-3-Hydroxy-1-(3,4-methylenedioxyphenethyl) pyrrolidine (281 mg, 1.19 mmol) was dissolved in dichloromethane (8 ml). Triethylamine (162 mg, 1.60 mmol) and methanesulfonyl chloride (183 mg, 1.60 mmol) were added to the obtained solution under stirring under cooling on ice. They were stirred at 0° C. for 1 hour. The reaction liquid was distributed in dichloromethane and water. The organic layer was dried, and the solvent was evaporated under reduced pressure. The obtained residue was subjected to silica gel column chromatography. The product was eluted with dichloromethane and then with a solvent mixture of dichloromethane and methanol (50:1). The appropriate fractions were combined, and the solvent was evaporated under reduced pressure to obtain (S)-3-methanesulfonyloxy-1-(3,4-methylenedioxyphenethyl) pyrrolidine in the form of a light yellow oil (359 mg, 97%).

NMR (CDCl$_3$) δ: 2.04–2.15 (1H, m), 2.26–2.38 (1H, m), 2.45–2.53 (1H, m), 2.63–2.76 (4H, m), 2.81–2.98 (3H, m), 3.02 (3H, s), 5.18–5.25 (1H, m), 5.92 (2H, s), 6.63–6.74 (3H, m)

(R)-5,11-Dihydro-5-[1-(3,4-methylenedioxyphenethyl) pyrrolidine-3-yl]dibenzo[b,e][1,4]oxazepine 60% sodium hydride (46 mg, 1.15 mmol) was washed with hexane under argon atmosphere, and then suspended in dimethyl sulfoxide (6 ml). After stirring at room temperature for 25 minutes, 5,11-dihydrodibenzo[b,e][1,4]oxazepine (197 mg, 1.0 mmol) was added to the obtained suspension. They were stirred at room temperature for 25 minutes and then at 50° C. for 25 minutes. A solution of (S)-3-methanesulfonyloxy-1-(3,4-methylenedioxyphenethyl) pyrrolidine (359 mg, 1.15 mmol) in dimethyl sulfoxide (3 ml) was added dropwise in the obtained solution, and they were stirred at 50° C. for 90 minutes. The reaction liquid was poured into ice/water. After the extraction with ethyl acetate, the organic layer was dried and the solvent was evaporated under reduced pressure. The obtained residue was subjected to silica gel column chromatography. The product was eluted with hexane and ethyl acetate (2:1) and then with hexane and ethyl acetate (1:2) as the eluents. The appropriate fractions were combined, and the solvent was evaporated under reduced pressure to obtain (R)-5,11-dihydro-5-[1-(3,4-methylene-dioxyphenethyl)pyrrolidine-3-yl]dibenzo[b,e][1,4]oxazepine in the form of a light yellow oil (63 mg, 15%).

NMR (CDCl$_3$) δ: 1.74–1.85 (1H, m), 2.21–2.35 (1H, m), 2.38–2.44 (1H, m), 2.49–2.59 (2H, m), 2.61–2.72 (3H, m), 2.77–2.85 (1H, m), 3.18–3.27 (1H, m), 4.66–4.75 (1H, m), 5.35 (1H, b), 5.43 (1H, b), 5.91 (2H, s), 6.60–6.84 (6H, m), 6.94–6.97 (1H, m), 7.05–7.13 (2H, m), 7.26–7.34 (2H, m)

(R)-5,11-Dihydro-5-[1-(3,4-methylenedioxyphenethyl) pyrrolidine-3-yl]dibenzo[b,e][1,4]oxazepine Hydrochloride 3.0 ml of 2 M hydrochloric acid/ethyl ether was added to a solution of (R)-5,11-dihydro-5-[1-(3,4-methylenedioxyphenethyl) pyrrolidine-3-yl]dibenzo[b,e][1,4]oxazepine (63 mg, 0.15 mmol) in dichloromethane, and they were stirred for 1 hour. The solvent was evaporated under reduced pressure to obtain the title compound in the form of a white solid (62 mg, 91%).

Melting point: 229–231° C.

ESI/Mass: 401 [M+H$^+$]

NMR (DMSO) δ: 1.80 (1H, b), 1.96 (1H, b), 2.33 (1H, b), 2.84–2.94 (4H, b), 3.16 (1H, b), 3.49 (1H, b), 3.56 (1H, b), 3.93 (1H, b), 4.93 (1H, b), 5.04 (1H, b), 5.97 (2H, s), 6.67–6.70 (2H, m), 6.76–6.84 (4H, m), 6.98–7.24 (3H, m), 7.35–7.48 (2H, m)

Example 13

(R)-5-[1-(4-chlorophenethyl)pyrrolidine-3-yl]-5,11-dihydrodibenzo[b,e][1,4] oxazepine Hydrochloride (S)-1-(4-Chlorophenethyl)-3-(4-nitrobenzoyloxy)pyrrolidine 4-Chlorophenethyl tosylate (683 mg, 2.20 mmol), sodium carbonate (236 mg, 2.20 mmol) and sodium iodide (20 mg, 0.13 mmol) were added to a solution of (S)-3-(4-nitrobenzoyloxy)pyrrolidine (472 mg, 2.00 mmol) in acetonitrile (10 ml), and they were heated under reflux at 90° C. for 8 hours. The solvent was evaporated under reduced pressure. The obtained residue was subjected to silica gel column chromatography. The product was eluted with hexane and ethyl acetate (10:1) and then with a mixture of the same solvents (1:1). The appropriate fractions were combined, and the solvent was evaporated under reduced pressure to obtain (S)-1-(4-chlorophenethyl)-3-(4-nitrobenzoyloxy)pyrrolidine in the form of a light yellow oil (315 mg, 42%).

NMR (CDCl$_3$) δ: 1.99–2.09 (1H, m), 2.33–2.56 (3H, m), 2.64–2.84 (4H, m), 2.90–2.97 (2H, m), 5.42–5.49 (1H, m), 7.14 (2H, d, J=9.3 Hz), 7.24 (2H, d, J=9.3 Hz), 8.21 (2H, d, J=9.7 Hz), 8.29 (2H, d, J=9.7 Hz)

(S)-1-(4-Chlorophenethyl)-3-hydroxypyrrolidine (S)-1-(4-Chlorophenethyl)-3-(4-nitrobenzoyloxy)pyrrolidine (315 mg, 0.84 mmol) was dissolved in methanol (10 ml). 1 M-NaOH (1 ml) was added dropwise in the obtained mixture. After stirring at room temperature for 1 hour, the solvent was evaporated under reduced pressure. The residue was distributed in water and ethyl acetate. The organic layer was dried, and the solvent was evaporated under reduced pressure to obtain (S)-1-(4-chlorophenethyl)-3-hydroxypyrrolidine in the form of a light yellow oil (190 mg, 100%).

NMR (CDCl$_3$) δ: 1.75–1.85 (1H, m), 2.16–2.27 (1H, m), 2.36–2.44 (1H, m), 2.58–2.63 (1H, m), 2.72–2.86 (5H, m), 2.99–3.06 (1H, m), 4.32–4.38 (1H, m), 6.83 (2H, d, J=9.7 Hz), 7.12 (2H, d, J=9.7 Hz)

(S)-1-(4-Chlorophenethyl)-3-methanesulfonyloxypyrrolidine (S)-1-(4-Chlorophenethyl)-3-hydroxypyrrolidine (190 mg, 0.84 mmol) was dissolved in dichloromethane (6 ml). Triethylamine (110 mg, 1.09 mmol) and methanesulfonyl chloride (125 mg, 1.09 mmol) were added to the obtained solution under stirring under cooling on ice. They were stirred at 0° C. for 1 hour. The reaction liquid was distributed in dichloromethane and water. The organic layer was dried, and the solvent was evaporated under reduced pressure. The obtained residue was subjected to silica gel column chromatography. The product was eluted with dichloromethane and then with a solvent mixture of dichloromethane and methanol (50:1). The appropriate fractions were combined, and the solvent was evaporated under reduced pressure to obtain (S)-1-(4-chlorophenethyl)-3-methanesulfonyloxypyrrolidine in the form of a light yellow oil (252 mg, 99%).

NMR (CDCl$_3$) δ: 2.04–2.15 (1H, m), 2.26–2.37 (1H, m), 2.45–2.53 (1H, m), 2.66–2.99 (7H, m), 3.01 (3H, s), 5.17–5.25 (1H, m), 7.14 (2H, d, J=9.3 Hz), 7.24 (2H, d, J=9.3 Hz)

(R)-5-[1-(4-chlorophenethyl)pyrrolidine-3-yl]-5,11-dihydrodibenzo[b,e][1,4]oxazepine 60% sodium hydride (34 mg, 0.87 mmol) was washed with hexane under argon atmosphere, and then suspended in dimethyl sulfoxide (4 ml). After stirring at room temperature for 25 minutes, 5,11-dihydrodibenzo[b,e][1,4]oxazepine (152 mg, 0.77 mmol) was added to the obtained suspension. They were stirred at room temperature for 25 minutes and then at 50° C. for 25 minutes. A solution of (S)-1-(4-chlorophenethyl)-3-methanesulfonyloxypyrrolidine (252 mg, 0.83 mmol) in dimethyl sulfoxide (2 ml) was added dropwise in the obtained solution, and they were stirred at 50° C. for 90 minutes. The reaction liquid was poured into water in ice cooling bath. After the extraction with ethyl acetate, the organic layer was dried and the solvent was evaporated under reduced pressure. The obtained residue was subjected to silica gel column chromatography. The product was eluted with hexane and ethyl acetate (2:1) and then with hexane and ethyl acetate (1:2) as the eluents. The appropriate fractions were combined, and the solvent was evaporated under reduced pressure to obtain (R)-5-[1-(4-chlorophenethyl) pyrrolidine-3-yl]-5,11-dihydrodibenzo[b,e][1,4]oxazepine in the form of a light yellow oil (44 mg, 14%).

NMR (CDCl$_3$) δ: 1.75–1.85 (1H, m), 2.05–2.15 (1H, m), 2.24–2.38 (1H, m), 2.41–2.55 (1H, m), 2.66–2.99 (6H, m), 4.66–4.74 (1H, m), 5.35 (1H, b), 5.42 (1H, b), 6.72–6.85 (2H, m), 7.05–7.12 (5H, m), 7.21–7.34 (5H, m)

(R)-5-[1-(4-Chlorophenethyl)pyrrolidine-3-yl]-5,11-dihydrodibenzo [b,e][1,4]oxazepine Hydrochloride 2.0 ml of 2 M hydrochloric acid/ethyl ether was added to a solution of (R)-5-[1-(4-chlorophenethyl)pyrrolidine-3-yl]-5,11-dihydro-dibenzo[b,e][1,4]oxazepine (44 mg, 0.11 mmol) in dichloromethane, and they were stirred for 1 hour. The solvent was evaporated under reduced pressure to obtain the title compound in the form of a light yellow solid (42 mg, 87%).

Melting point: 238–240° C.

ESI/Mass: 401 [M+H$^+$]

NMR (DMSO) δ: 1.80 (1H, b), 1.98 (1H, b), 2.30 (1H, b), 2.94–2.99 (4H, m), 3.39 (2H, b), 3.52 (1H, b), 3.59 (1H, b), 4.93 (1H, b), 5.05 (1H, b), 6.68–6.89 (3H, m), 6.99–7.29 (5H, m), 7.37–7.49 (4H, m)

Example 14

5,11-Dihydro-5-[2-[N-(4-methoxyphenethyl)-N-methylamino]ethyl]dibenzo[b,e][1,4]oxazepine Hydrochloride 5,11-Dihydro-5-(ethoxycarbomethyl)dibenzo[b,e][1,4]oxazepine 60% sodium hydride (0.99 g, 24 mmol) was washed with hexane under argon atmosphere, and then suspended in dimethyl sulfoxide (5.0 ml). 5,11-Dihydrodibenzo[b,e][1,4]oxazepine (4.0 g, 20.3 mmol) was added to the obtained suspension. They were stirred at room temperature for 90 minutes. A solution of ethyl bromoacetate (5.01 g, 30 mmol) in dimethyl sulfoxide (10 ml) was added dropwise in the obtained solution, and they were stirred at room temperature for 60 minutes and then at 40° C. for 3 hours. The reaction liquid was poured into 5% aqueous potassium hydrogensulfate solution. After the extraction with ethyl acetate, the organic layer was washed with saturated aqueous sodium hydrogencarbonate solution and then with saturated aqueous sodium chloride solution. After drying, the solvent was evaporated under reduced pressure. The obtained residue was subjected to silica gel column chromatography. The product was eluted with hexane and then with ethyl acetate and hexane (1:11). The appropriate fractions were combined, and the solvent was evaporated under reduced pressure to obtain 5,11-dihydro-5-(ethoxycarbomethyl)dibenzo[b,e][1,4]oxazepine in the form of a light yellow solid (2.29 g, 40.5%).

NMR (CDCl$_3$) δ: 1.14 (3H, t, J=8.0 Hz), 4.13 (2H, q, J=8.0 Hz), 4.49 (2H, s), 5.29 (2H, s), 6.75–6.86 (3H, m), 6.90–7.12 (3H, m), 7.16–7.28 (2H, m)

5,11-Dihydro-5-(2-hydroxyethyl)dibenzo[b,e][1,4]oxazepine 0.76 g (20 mmol) of lithium aluminum hydride was suspended in 20 ml of dry ether under argon atmosphere. A solution of 5,11-dihydro-5-(ethoxycarbomethyl)dibenzo[b,e][1,4]oxazepine (2.29 g, 8.09 mmol) in dry ether (20 ml) was added dropwise into the suspension at a rate capable of keeping mild reflux of ether. After reflux at 40° C. for 3 hours, the reaction mixture was cooled to room temperature. 3 ml of saturated anhydrous sodium sulfate solution and 6 ml of ethyl acetate were added to the reaction mixture. Precipitates were removed by the filtration, and the solvent was evaporated under reduced pressure. The obtained residue was subjected to silica gel column chromatography. The product was eluted with a solvent mixture of ethyl acetate and hexane (1:3). The appropriate fractions were combined, and the solvent was evaporated under reduced pressure to obtain 5,11-dihydro-5-(2-hydroxyethyl) dibenzo[b,e][1,4]oxazepine in the form of a light yellow oil (0.99 g, 51%).

NMR (CDCl$_3$) δ: 1.76 ((1H, b), 3.78 (2H, t, J-6.3 Hz), 3.93 (2H, t, J=6.3 Hz), 5.31 (2H, s), 6.75–6.85 (3H, m), 6.93–7.10 (3H, m), 7.20–7.32 (2H, m)

5,11-Dihydro-5-[2-(4-methylphenylsulfonyl)oxyethyl]dibenzo[b,e][1,4]oxazepine 0.99 g (4.1 mmol) of 5,11-dihydro-5-(2-hydroxyethyl)dibenzo[b,e][1,4]oxazepine was dissolved in 6 ml of anhydrous pyridine. 0.94 g (4.9 mmol) of p-toluenesulfonyl chloride was added to the obtained solution, and they were stirred at room temperature for 6 hours. The solvent was evaporated under reduced pressure. The residue was dissolved in dichloromethane. The obtained solution was washed with 5% aqueous potassium hydrogensulfate solution, saturated aqueous sodium hydrogencarbonate solution and saturated aqueous sodium chloride solution successively. After drying, the solvent was evaporated under reduced pressure. The obtained residue was subjected to silica gel column chromatography. The product was eluted with ethyl acetate and hexane (1:3). The appropriate fractions were combined, and the solvent was evaporated under reduced pressure to obtain 5,11-dihydro-5-[2-(4-methylphenylsulfonyl)oxyethyl]dibenzo[b,e][1,4]oxazepine in the form of a light yellow oil (1.25 g, 76.6%).

NMR (CDCl$_3$) δ: 2.40 (3H, s), 4.02 (2H, t, J-6.3 Hz), 4.21 (2H, t, J=6.3 Hz), 5.33 (2H, s), 6.72–6.85 (4H, m), 6.97–7.06 (2H, m), 7.20–7.30 (2H, m)

7.24 (2H, d, J=9.0 Hz), 7.64 (2H, d, J=9.0 Hz)

5,11-Dihydro-5-[2-[N-(4-methoxyphenethyl)-N-methylamino]ethyl]dibenzo[b,e][1,4]oxazepine 5,11-Dihydro-5-[2-(4-methylphenylsulfonyl)oxyethyl]dibenzo [b,e][1,4]oxazepine (650 mg, 1.65 mmol), N-methyl-4-methoxyphenethylamine (290 mg, 1.76 mmol), sodium carbonate (195 mg, 1.84 mmol) and sodium iodide (25 mg, 0.17 mmol) were added to acetonitrile (20 ml), and they were heated under reflux at 90° C. for 6 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with ethyl acetate and hexane (6:1) and then with the same solvents (1:1). The appropriate fractions were combined, and the solvent was evaporated under reduced pressure to obtain 5,11-dihydro-5-[2-[N-(4-methoxyphenethyl)-N-methylamino]ethyl]dibenzo[b,e][1,4]oxazepine in the form of a light yellow oil (423 mg, 66%).

NMR (CDCl$_3$) δ: 2.30 (3H, s), 2.51–2.62 (4H, m), 2.64 (2H, t, J=7.7 Hz), 3.78 (3H, s), 3.88 (2H, t, J=7.7 Hz), 5.27 (2H, s), 6.75–6.88 (5H, m), 7.01–7.16 (5H, m), 7.28–7.35 (2H, m)

5,11-Dihydro-5-[2-[N-(4-methoxyphenethyl)-N-methylamino]ethyl]dibenzo[b,e][1,4]oxazepine Hydrochloride 3 ml of 4 M hydrochloric acid/dioxane was added to a solution of 5,11-dihydro-5-[2-[N-(4-methoxyphenethyl)-N-methylamino]ethyl]dibenzo[b,e][1,4]oxazepine (423 mg, 1.09 mmol) in dichloromethane (10 ml), and they were stirred for 1 hour. The solvent was evaporated under reduced pressure. The residue was recrystallized from a solvent mixture of ethyl acetate and hexane to obtain the title compound in the form of a white solid (389 mg, 84%).

Melting point: 139–140° C.

ESI/Mass: 389 [M+H$^+$]

NMR (CD$_3$OD) δ: 2.85–2.94 (2H, b), 2.96 (3H, s), 3.32–3.40 (2H, b), 3.40–3.48 (2H, b), 3.76 (3H, b), 4.21 (2H, t, J=1.7 Hz), 5.28 (2H, s), 6.79–6.93 (3H, m), 6.84 (2H, d, J=7.3 Hz), 7.07–7.15 (2H, m), 7.09 (2H, d, J=7.3 Hz), 7.23–7.42 (3H, m)

Example 15

5,11-Dihydro-5-[2-[N-(3-methoxyphenethyl)-N-methylamino]ethyl]dibenzo[b,e][1,4]oxazepine Hydrochloride 5,11-Dihydro-5-(carboxymethyl)dibenzo[b,e][1,4]oxazepine 60% sodium hydride (3.60 g, 90 mmol) was washed with hexane under argon atmosphere, and then suspended in dimethyl sulfoxide (130 ml). 5,11-Dihydrodibenzo[b,e][1,4]oxazepine (14.8 g, 75.0 mmol) was added to the obtained suspension. They were stirred at room temperature for 60 minutes. A solution of ethyl bromoacetate (16.7 g, 150 mmol) in dimethyl sulfoxide (30 ml) was added dropwise in the obtained solution, and they were stirred at room temperature for 70 minutes and then at 50° C. for 2 hours. The reaction liquid was poured into 5% aqueous potassium hydrogensulfate solution. After the extraction with ethyl acetate, the organic layer was washed with saturated aqueous sodium hydrogencarbonate solution and then with saturated aqueous sodium chloride solution. After drying, the solvent was evaporated under reduced pressure. The obtained residue was dissolved in 200 ml of methanol. 200 ml of 4 M aqueous sodium hydroxide solution was added to the obtained solution, and they were stirred at room temperature for 1 hour. After the extraction with ethyl acetate, 40 ml of 6 M hydrochloric acid was added to the aqueous layer to adjust pH to 1. After the extraction with ethyl acetate, the organic layer was washed with saturated aqueous sodium hydrogencarbonate solution and then with saturated aqueous sodium chloride solution. After drying, the solvent was evaporated under reduced pressure. The obtained residue was subjected to silica gel column chromatography. The product was eluted with ethyl acetate and hexane (5:1) and then with ethyl acetate and hexane (1:3). The appropriate fractions were combined, and the solvent was evaporated under reduced pressure to obtain 5,11-dihydro-5-(carboxymethyl)dibenzo[b,e][1,4] oxazepine in the form of a light yellow solid (6.40 g, 33.5%).

ESI/Mass: 256 [M+H$^+$]

NMR (CDCl$_3$) δ: 4.60 (2H, s), 5.32 (2H, s), 6.85–6.92 (4H, m), 7.04–7.11 (2H, m), 7.25–7.34 (2H, m)

5,11-Dihydro-5-(N-methylcarboxamidomethyl)dibenzo[b,e][1,4]oxazepine 5,11-Dihydro-5-(carboxymethyl)dibenzo[b,e][1,4]oxazepine (6.40 g, 25.1 mmol) was dissolved in 150 ml of dichloromethane. 25 ml of 2 M solution of oxalyl chloride in dichloromethane and 5 drops of dimethyl formamide were added to the obtained solution, and they were stirred at room temperature for 2 hours. The obtained solution was added dropwise in 50 ml of 2 M solution of methylamine in tetrahydrofuran under stirring and cooling on ice. They were stirred under cooling on ice for 90 minutes. The obtained solution was washed with saturated aqueous sodium hydrogencarbonate solution. The organic layer was dried, and the solvent was evaporated under reduced pressure. The obtained residue was subjected to silica gel column chromatography. The product was eluted with dichloromethane and then with dichloromethane and methanol (20:1). The appropriate fractions were combined, and the solvent was evaporated under reduced pressure to obtain 5,11-dihydro-5-(N-methylcarboxamidomethyl)dibenzo [b,e][1,4]oxazepine in the form of a light yellow solid (4.05 g, 60.2%).

ESI/Mass: 269 [M+H$^+$]

NMR (CDCl$_3$) δ: 2.78 (3H, d, J=5.0 Hz), 4.44 (2H, s), 5.29 (2H, s), 6.50 (1H, b), 6.92–7.09 (6H, m), 7.13–7.29 (2H, m)

5,11-Dihydro-5-[2-(N-methylamino)ethyl] dibenzo[b,e][1,4]oxazepine 2.48 g (64 mmol) of lithium aluminum hydride was suspended in 100 ml of dry tetrahydrofuran under argon atmosphere. A solution of 5,11-dihydro-5-(N-methylcarboxamido)methyldibenzo[b,e][1,4]oxazepine (4.04 g, 15.1 mmol) in dry tetrahydrofuran (30 ml) was added dropwise in the obtained suspension at room temperature. After reflux under heating for 4 hours followed by the cooling to room temperature, 3 ml of saturated anhydrous sodium sulfate solution and 150 ml of ethyl acetate were added thereto, and they were thoroughly stirred. The precipitates thus formed were filtered out, and the solvent was evaporated under reduced pressure. The residue was dissolved in dichloromethane. After the extraction with 0.2 M hydrochloric acid, 22 ml of 4 M aqueous sodium hydroxide solution was added to the aqueous layer to adjust pH thereof to 11. After the extraction with dichloromethane, the organic layer was dried. The solvent was evaporated under reduced pressure to obtain 5,11-dihydro-5-[2-(n-methylamino)ethyl]dibenzo[b,e][1,4]oxazepine in the form of a light yellow oil (2.26 g, 56%).

ESI/Mass: 255 [M+H$^+$]

NMR (CDCl$_3$) δ: 1.56 ((1H, b), 2.38 (3H, s), 2.84 (2H, t, J=7.0 Hz), 3.89 (2H, t, J=7.0 Hz), 5.31 (2H, s), 6.78–6.84 (2H, m), 7.02–7.14 (4H, m), 7.26–7.31 (2H, m)

5,11-Dihydro-5-[2-[N-(3-methoxyphenethyl)-N-methylamino]ethyl]dibenzo[b,e][1,4]oxazepine 5,11-Dihydro-5-[2-(N-methylamino)ethyl]dibenzo[b,e][1,4]oxazepine (349 mg, 1.37 mmol), 3-methoxyphenethyl mesylate (450 mg, 1.96 mmol), sodium carbonate (208 mg, 1.96 mmol) and sodium iodide (20 mg, 0.13 mmol) were added to acetonitrile (25 ml), and they were heated under reflux at 90° C. for 6 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The obtained residue was subjected to silica gel column chromatography. The product was eluted with dichloromethane and hexane (1:2) and then with dichloromethane as the eluent. The appropriate fractions were combined, and the solvent was evaporated under reduced pressure to obtain 5,11-dihydro-5-[2-[N-(3-methoxyphenethyl)-N-methylamino]ethyl]dibenzo[b,e][1,4]oxazepine in the form of a light yellow oil (275 mg, 52%).

NMR (CDCl$_3$) δ: 2.30 (3H, s), 2.55–2.64 (4H, m), 2.64 (2H, t, J=8.0 Hz), 3.71 (3H, s), 3.88 (2H, t, J=8.0 Hz), 5.27 (2H, s), 6.67–6.84 (6H, m), 7.00–7.05 (2H, m), 7.11–7.33 (4H, m)

5,11-Dihydro-5-[2-[N-(3-methoxyphenethyl)-N-methylamino]ethyl]dibenzo [b,e][1,4]oxazepine Hydrochloride 5 ml of 2 M hydrochloric acid/ethyl ether was added to 5,11-dihydro-5-[2-[N-(3-methoxyphenethyl)-N-methylamino]ethyl]dibenzo [b,e][1,4]oxazepine (275 mg, 0.71 mmol), and they were stirred for 1 hour. The solvent was evaporated under reduced pressure to obtain the title compound in the form of a yellow solid (220 mg, 73%).

ESI/Mass: 389 [M+H$^+$]

NMR (CDCl$_3$) δ: 2.84 (3H, d, J=5.3 Hz), 3.07–3.20 (4H, m), 3.37–3.41 (2H, m), 3.77 (3H, s), 4.25–4.34 (2H, m), 4.41–4.50 (2H, m), 5.21 (2H, s), 6.72–6.93 (6H, m), 7.06–7.11 (2H, m), 7.17–7.26 (3H, m), 7.33–7.38 (1H, m)

Example 16

5,11-Dihydro-5-[2-[N -[3-(4-methoxyphenyl)propyl]-N-methylamino]ethyl]dibenzo[b,e][1,4] oxazepine Hydrochloride 5,11-Dihydro-5-[2-[N-[3-(4-methoxyphenyl)propyl]-N-methylamino]ethyl]dibenzo[b,e][1,4]oxazepine 5,11-Dihydro-5-[2-(N-methylamino)ethyl]dibenzo[b,e][1,4]oxazepine (245 mg, 0.96 mmol), 3-(4-methoxyphenyl)propyl mesylate (353 mg, 1.45 mmol), sodium carbonate (154 mg, 1.45 mmol) and sodium iodide (20 mg, 0.13 mmol) were added to acetonitrile (25 ml), and they were heated under reflux at 90° C. for 6 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with dichloromethane and hexane (1:2) and then with dichloromethane. The appropriate fractions were combined, and the solvent was evaporated under reduced pressure to obtain 5,11-dihydro-5-[2-[N-[3-(4-methoxyphenyl)propyl]-N-methylamino]ethyl]dibenzo[b,e][1,4]oxazepine in the form of a light yellow oil (101 mg, 26%).

NMR (CDCl$_3$) δ: 1.66 (2H, q, J=8.3 Hz), 2.21 (3H, s), 2.31 (2H, t, J=8.3 Hz), 2.49 (2H, t, J=8.3 Hz), 2.58 (2H, t, J=7.7 Hz), 3.78 (3H, s), 3.86 (2H, t, J=7.7 Hz), 5.30 (2H, s), 6.77–6.85 (5H, m), 7.00–7.05 (4H, m), 7.11–7.34 (3H, m)

5,11-Dihydro-5-[2-[N-[3-(4-methoxyphenyl)propyl]-N-methylamino]ethyl]dibenzo[b,e][1,4]oxazepine Hydrochloride 5 ml of 2 M hydrochloric acid/ethyl ether was added to 5,11-dihydro-5-[2-[N-[3-(4-methoxyphenyl)propyl]-N-methylamino]ethyl]dibenzo[b,e][1,4]oxazepine(101 mg, 0.25 mmol), and they were stirred for 1 hour. The solvent was evaporated under reduced pressure to obtain the title compound in the form of a yellow solid (84 mg, 77%).

ESI/Mass: 389 [M+H$^+$]

NMR (CDCl$_3$) δ: 2.20–2.22 (2H, m), 2.55–2.70 (4H, m), 2.75 (3H, d, J=5.0 Hz), 2.81–2.91 (1H, m), 3.01–3.16 (2H, m), 3.21–3.31 (1H, m), 3.78 (3H, s), 4.21–4.42 (2H, m), 5.23 (1H, d, J=14.0 Hz), 5.25 (1H, d, J=14.0 Hz), 6.78–6.92 (5H, m), 7.00–7.18 (4H, m), 7.25–7.38 (3H, m)

Example 17

5,11-Dihydro-5-[2-[N-methyl-N-(3,4-methylenedioxyphenethyl) amino]ethyl]dibenzo[b,e][1,4]oxazepine Hydrochloride 5,11-Dihydro-5-[2-[N-methyl-N-(3,4-methylenedioxyphenethyl) amino]ethyl]dibenzo[b,e][1,4]oxazepine 5,11-Dihydro-5-[2-(N-methylamino)ethyl]dibenzo[b,e][[1,4]oxazepine (254 mg, 1.00 mmol), 3,4-methylenedioxyphenethyl mesylate (366 mg, 1.50 mmol), sodium carbonate (160 mg, 1.50 mmol) and sodium iodide (20 mg, 0.13 mmol) were added to acetonitrile (25 ml), and they were heated under stirring at 70° C. for 22 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with dichloromethane and hexane (1:2), then with dichloromethane and finally with dichloromethane and methanol (100:1). The appropriate fractions were combined, and the solvent was evaporated under reduced pressure to obtain 5,11-dihydro-5-[2-[N-methyl-N-(3,4-methylenedioxyphenethyl) amino]ethyl]dibenzo[b,e][1,4]oxazepine in the form of a light yellow oil (282 mg, 70%).

NMR (CDCl$_3$) δ: 2.28 (3H, s), 2.49–2.60 (4H, m), 2.63 (2H, t, J=7.7 Hz), 3.87 (2H, t, J=7.7 Hz), 5.27 (2H, s), 5.91 (2H, s), 6.54–6.85 (6H, m), 7.00–7.13 (3H, m), 7.25–7.34 (2H, m)

5,11-Dihydro-5-[2-[N-methyl-N-(3,4-methylenedioxyphenethyl) amino]ethyl]dibenzo[b,e][1,4]oxazepine Hydrochloride 5 ml of 2 M hydrochloric acid/ethyl ether was added to 5,11-dihydro-5-[2-[N-(3,4-methylenedioxyphenethyl)-N-methylamino]ethyl]dibenzo[b,e][1,4]oxazepine (282 mg, 0.70 mmol), and they were stirred for 1 hour. The solvent was evaporated under reduced pressure to obtain the title compound in the form of a yellow solid (246 mg, 80%).

ESI/Mass: 389 [M+H$^+$]

NMR (CDCl$_3$) δ: 2.83 (3H, d, J=3.7 Hz), 3.01–3.18 (4H, m), 3.27–3.40 (2H, m), 4.24–4.34 (2H, m), 4.39–4.49 (2H, m), 5.23 (2H, s), 5.93 (2H, s), 6.60–6.72 (3H, m), 6.83–6.93 (3H, m), 7.06–7.11 (2H, m), 7.18–7.28 (2H, m), 7.34–7.39 (1H, m)

Example 18

5-[2-[N-(4-chlorophenethyl)-N-methylamino]ethyl]-5,11-dihydrodibenzo [b,e][1,4]oxazepine Hydrochloride 5-[2-[N-(4-chlorophenethyl)-N-methylamino]ethyl]-5,11-dihydrodibenzo [b,e][1,4]oxazepine 5,11-Dihydro-5-[2-(N-methylamino)ethyl]dibenzo[b,e][1,4]oxazepine (254 mg, 1.00 mmol), 4-chlorophenethyl mesylate (352 mg, 1.50 mmol), sodium carbonate (160 mg, 1.50 mmol) and sodium iodide (20 mg, 0.13 mmol) were added to acetonitrile (25 ml), and they were heated at 70° C. under stirring for 22 hours and then at 90° C. under reflux for 6 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with dichloromethane and then with dichloromethane and methanol (100:1). The appropriate fractions were combined, and the solvent was evaporated under reduced pressure to obtain 5-[2-[N-(4-chlorophenethyl)-N-methyl-amino]ethyl]-5,11-dihydrodibenzo[b,e][1,4]oxazepine in the form of a light yellow oil (171 mg, 44%).

NMR (CDCl$_3$) δ: 2.28 (3H, s), 2.53–2.61 (4H, m), 2.63 (2H, t, J=7.7 Hz), 3.85 (2H, t, J=7.7 Hz), 5.25 (2H, s), 6.67–6.84 (3H, m), 6.99–7.12 (5H, m), 7.19–7.33 (4H, m)

5-[2-[N-(4-chlorophenethyl)-N-methylamino]ethyl]-5,11-dihydrodibenzo [b,e][1,4]oxazepine Hydrochloride 5 ml of 2 M hydrochloric acid/ethyl ether was added to 5-[2-[N-(4-chlorophenethyl)-N-methylamino]ethyl]-5,11-dihydrodibenzo[b,e][1,4]oxazepine (282 mg, 0.70 mmol), and they were stirred for 1 hour. The solvent was evaporated under reduced pressure. The obtained residue was recrystallized from a solvent mixture of dichloromethane and ethyl ether to obtain the title compound in the form of light green crystals (163 mg, 87%).

Melting point: 188–191° C.

ESI/Mass: 389 [M+H$^+$]

NMR (CDCl$_3$) δ: 2.84 (3H, d, J=5.3 Hz), 3.08–3.22 (4H, m), 3.26–3.39 (2H, m), 4.24–4.34 (1H, m), 4.42–4.52 (1H, m), 5.21 (2H, s), 6.83–6.95 (3H, m), 7.05–7.11 (4H, m), 7.17–7.27 (4H, m), 7.33–7.39 (1H, m)

Example 19

5,11-Dihydro-5-[2-[N-(4-dimethylaminophenethyl)-N-methylamino]ethyl]dibenzo[b,e][1,4]oxazepine Dihydrochloride 5,11-Dihydro-5-[2-[N-(4-dimethylaminophenethyl)-N-methylamino]ethyl]dibenzo[b,e][1,4]oxazepine 5,11-Dihydro-5-[2-(N-methylamino)ethyl]dibenzo[b,e][1,4]oxazepine (254 mg, 1.00 mmol), 4-dimethylaminophenethyl mesylate (365 mg, 1.50 mmol), sodium carbonate (160 mg, 1.50 mmol) and sodium iodide (20 mg, 0.13 mmol) were added to acetonitrile (20 ml), and they were heated under reflux at 90° C. for 7 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with dichloromethane and then with dichloromethane and methanol (100:1). The appropriate fractions were combined, and the solvent was evaporated under reduced pressure to obtain 5,11-dihydro-5-[2-[N-(4-dimethylaminophenethyl)-N-methylamino]ethyl]dibenzo[b,e][1,4]oxazepine in the form of a light yellow oil (184 mg, 46%).

NMR (CDCl$_3$) δ: 2.30 (3H, s), 2.50–2.61 (4H, m), 2.65 (2H, t, J=8.0 Hz), 2.90 (6H, s), 3.89 (2H, t, J=8.0 Hz), 5.28 (2H, s), 6.64–6.68 (2H, m), 6.77–6.85 (3H, m), 6.98–7.14 (5H, m), 7.25–7.34 (2H, m)

5,11-Dihydro-5-[2-[N-(4-dimethylaminophenethyl)-N-methylamino]ethyl]dibenzo[b,e][1,4]oxazepine Dihydrochloride 5 ml of 2 M hydrochloric acid/ethyl ether was added to 5,11-dihydro-5-[2-[N-(4-dimethylaminophenethyl)-N-methylamino]ethyl]dibenzo[b,e][1,4]oxazepine (184 mg, 0.46 mmol), and they were stirred for 1 hour. The solvent was evaporated under reduced pressure to obtain the title compound in the form of light green crystals (194 mg, 89%).

Melting point: 111–113° C.

ESI/Mass: 389 [M+H$^+$]

NMR (CDCl$_3$) δ: 2.88 (3H, d, J=5.0 Hz), 3.14 (6H, s), 3.16–3.28 (4H, m), 3.32–3.42 (2H, m), 4.23–4.33 (1H, m), 4.43–4.53 (1H, m), 5.22 (1H, d, J=14.0 Hz), 5.25 (1H, d, J=14.0 Hz), 6.84–6.95 (3H, m), 7.06–7.11 (2H, m), 7.17–7.25 (2H, m), 7.33–7.38 (3H, m), 7.68–7.70 (2H, m)

Example 20

5,11-Dihydro-5-[2-[N-(3-dimethylaminophenethyl)-N-methylamino]ethyl]dibenzo[b,e][1,4]oxazepine Dihydrochloride 5,11-Dihydro-5-[2-[N-(3-dimethylaminophenethyl)-N-methylamino]ethyl]dibenzo[b,e][1,4]oxazepine 5,11-Dihydro-5-[2-(N-methylamino)ethyl]dibenzo[b,e][[1,4]oxazepine (254 mg, 1.00 mmol), 3-dimethylaminophenethyl mesylate (312 mg, 1.30 mmol), sodium carbonate (140 mg, 1.30 mmol) and sodium iodide (20 mg, 0.13 mmol) were added to acetonitrile (20 ml), and they were heated under reflux at 90° C. for 10 hours. The solvent was evaporated under reduced pressure. The obtained residue was distributed in ethyl acetate and saturated aqueous sodium hydrogencarbonate solution. The organic layer was washed with water and then dried over magnesium sulfate. The solvent was evaporated under reduced pressure. The residue was subjected to silica gel column chromatography. The product was eluted with dichloromethane and then with dichloromethane and methanol (50:1). The appropriate fractions were combined, and the solvent was evaporated under reduced pressure to obtain 5,11-dihydro-5-[2-[N-(3-dimethylaminophenethyl)-N-methylamino]ethyl]dibenzo[b,e][1,4]oxazepine in the form of a light yellow oil (296 mg, 74%).

NMR (CDCl$_3$) δ: 2.32 (3H, s), 2.58–2.64 (4H, m), 2.66 (2H, t, J=7.7 Hz), 2.91 (6H, s), 3.89 (2H, t, J=7.7 Hz), 5.28 (2H, s), 6.48–6.62 (3H, m), 6.78–6.85 (3H, m), 6.96–7.05 (2H, m), 7.10–7.15 (2H, m), 7.25–7.33 (2H, m)

5,11-Dihydro-5-[2-[N-(3-dimethylaminophenethyl)-N-methylamino]ethyl]dibenzo[b,e][1,4]oxazepine Dihydrochloride 5 ml of 2 M hydrochloric acid/ethyl ether was added to 5,11-dihydro-5-[2-[N-(3-dimethylaminophenethyl)-N-methylamino]ethyl]dibenzo[b,e][1,4]oxazepine (296 mg, 0.74 mmol), and they were stirred for 1 hour. The solvent was evaporated under reduced pressure to obtain the title compound in the form of light green crystals (285 mg, 81%).

Melting point: 97–98° C.

ESI/Mass: 389 [M+H$^+$]

NMR (CDCl$_3$) δ: 2.89 (3H, d, J=2.7 Hz), 3.17 (6H, s), 3.20–3.32 (4H, m), 3.37–3.47 (2H, m), 4.22–4.32 (1H, m), 4.41–4.51 (1H, m), 5.24 (1H, d, J=14.0 Hz), 5.26 (1H, d, J=14.0 Hz), 6.82–6.93 (3H, m), 7.05–7.10 (2H, m), 7.17–7.26 (2H, m), 7.32–7.51 (3H, m), 7.62–7.91 (2H, m)

Preparation Examples will be given below.

Preparation Example 1

The following components are mixed together by an ordinary method and then tableted to obtain tablets containing 50 mg/tablet of the active ingredient:

| Compound of Example 1, 8 or 14 | 50 mg |
|---|---|
| Lactose | 200 mg |
| Crystalline cellulose | 40 mg |
| Magnesium stearate | 5 mg |

Preparation Example 2

The following components are mixed together by an ordinary method and then granulated to obtain granules:

| Compound of Example 1, 8 or 14 | 50 mg |
|---|---|
| Lactose | 90 mg |
| Corn starch | 60 mg |
| Talc | 30 mg |
| Magnesium stearate | 10 mg |

The description will be made below on the pharmacological tests of the compounds of the present invention.

Test Example 1

In vitro calcium channel antagonistic effect (blood vessel)

The thoracic aorta was extracted from each of male Crj:CD rats (8 to 12 weeks old) to prepare helical samples. The blood vessel samples were suspended in 37° C. Tyrode's solution through which a gaseous mixture (95% of oxygen and 5% of carbon dioxide) was passed. For examining the change in tensile strength of the blood vessel, the isometry thereof was recorded on a pen-writing recorder through a transducer. The high potassium contraction was caused by exchanging the nutrient solution from Tyrode's solution to potassium-Tyrode's solution (94.6 mM of NaCl, 45.0 mM of KCl, 1.8 mM of CaCl$_2$, 1.04 mM of MgCl$_2$, 0.4 mM of NaH$_2$PO$_4$, 11.9 mM of NaHCO$_3$ and 5.55 mM of glucose). The high potassium contraction-inhibiting effect of a test compound was evaluated by 30 minute pretreatment. Compound A described in European Patent No. 0404359A1 and compound B described in International Patent No. 9733885A1 were used as comparative substances. The calcium channel antagonistic activity was shown as the rate (%) of inhibition of control of high-calcium contraction with 10$^{-7}$ M test compound. The concentration of the test compounds for 50% contraction inhibition (IC$_{50}$) is also shown in Table 1.

TABLE 1

| Calcium channel antagonistic effect (blood vessel) | | |
|---|---|---|
| Test compound | Inhibition rate (%) (conc: 10$^{-7}$ M) | IC$_{50}$ (nM) |
| Example 1 | 38 | 165 |
| Example 3 | 33 | — |
| Example 4 | 32 | — |
| Example 5 | 27 | — |
| Example 6 | 25 | — |
| Example 7 | 23 | — |
| Example 8 | 52 | 92 |
| Example 10 | 59 | — |
| Example 11 | 61 | — |
| Example 12 | 51 | — |
| Example 13 | 38 | — |
| Example 14 | 43 | 119 |
| Example 15 | 29 | — |
| Example 16 | 28 | — |
| Example 17 | 30 | — |
| Example 18 | 34 | — |
| Example 19 | 39 | — |
| Example 20 | 28 | — |
| Compound A | 9 | 530 |
| Compound B | 17 | 241 |

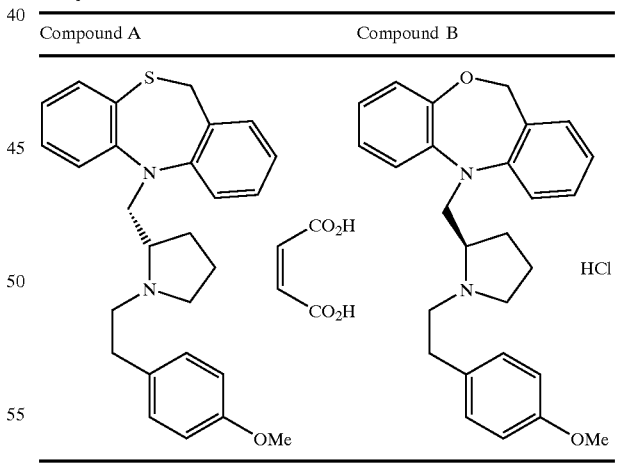

Compound A                Compound B

Test Example 2

In vitro calcium channel antagonistic effect (ileum)

The ileum of each of male Crj:CD rats (8 to 12 weeks old) was extracted at a part 3 cm apart from the ileocecal region. The ileum sample was suspended in 37° C. Tyrode's solution through which a gaseous mixture (95% of oxygen and 5% of carbon dioxide) was passed. For examining the change in tensile strength of the ileum, the isotonicity thereof was recorded on a pen-writing recorder through a transducer. The high potassium contraction was caused by exchanging the nutrient solution from Tyrode's solution to potassium-Tyrode's solution (94.6 mM of NaCl, 45.0 mM of KCl, 1.8 mM of $CaCl_2$, 1.04 mM of $MgCl_2$, 0.4 mM of $NaH_2PO_4$, 11.9 mM of $NaHCO_3$ and 5.55 mM of glucose). The high potassium contraction-inhibiting effect of a test compound was evaluated by 30 minute pretreatment. Compound A described in European Patent No. 0404359A1 and compound B described in International Patent No. 9733885A1 were used as comparative substances. The calcium channel antagonistic activity was shown as the rate (%) of inhibition of control of high-calcium contraction with $10^{-7}$ M test compound. The concentration of the test compounds for 50% contraction inhibition ($IC_{50}$) is also shown in Table 2.

TABLE 2

Calcium channel antagonistic effect (ileum)

| Test compound | Inhibition rate (%) (conc.: $10^{-7}$M) | $IC_{50}$(nM) |
|---|---|---|
| Example 1 | 90 | 44 |
| Example 3 | 61 | — |
| Example 4 | 64 | — |
| Example 5 | 66 | — |
| Example 6 | 75 | — |
| Example 7 | 78 | — |
| Example 8 | 100 | 18 |
| Example 10 | 116 | — |
| Example 11 | 83 | — |
| Example 12 | 77 | — |
| Example 13 | 76 | — |
| Example 14 | 105 | 35 |
| Example 15 | 82 | — |
| Example 16 | 82 | — |
| Example 17 | 78 | — |
| Example 18 | 70 | — |
| Example 19 | 76 | — |
| Example 20 | 50 | — |
| Compound A | 48 | 120 |
| Compound B | 67 | 46 |

It is apparent from the results shown in Tables 1 and 2 that the compounds of the present invention have an excellent calcium channel antagonistic effect and that they are useful as calcium channel antagonists having a particularly high selectivity toward intestinal tracts.

It is apparent from the Test Examples described above that the compounds of the present invention exhibit excellent effects as therapeutic agents and preventive drugs for abnormal motor functions of gastrointestinal tracts, particularly irritable bowel syndrome.

Modifications and other embodiments

Various modifications and variations of the described oxazepine derivatives, compositions and processes or methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the biological, chemical, medical or pharmacological arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specific incorporation is made to PCT/JP00/00071, filed Jan. 11, 2000 and to priority documents JP 11-3268, filed Jan. 8, 1999, JP 11-3269, filed Jan. 8, 1999, and JP 11-3270, filed Jan. 8, 1999.

What is claimed is:

1. A 5,11-Dihydrodibenzo[b,e][1,4]oxazepine compound of following formula [Ia], [Ib] or [Ic], a stereoisomer thereof, a pharmacologically acceptable salt thereof or a hydrate thereof:

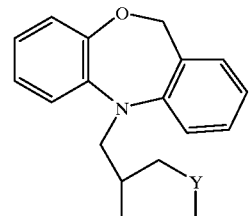

[Ia]

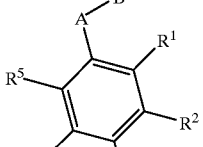

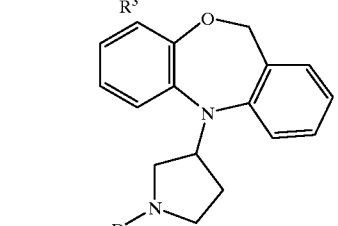

[Ib]

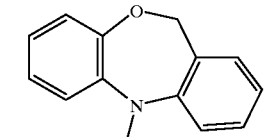

[Ic]

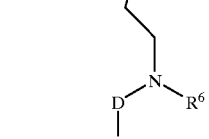

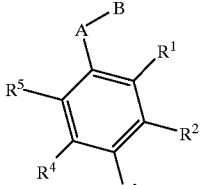

wherein $R^1$ to $R^5$ may be the same or different from each other and they each represent hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —O(CH$_2$)$_n$O— group (n being 1, 2 or 3), $R^6$ represents hydrogen or a lower alkyl group, Y represents methylene group, oxygen atom, sulfur atom or an alkylamino group, A represents CH$_2$, CHOH, CO or O, B represents CH$_2$, CHOH or CO, or A-B represents CH=CH, and D represents CH$_2$, CH$_2$—CH$_2$ or CH$_2$—CH$_2$—CH$_2$, or B-D represents CH$_2$.

2. The 5,11-Dihydrodibenzo[b,e][1,4]oxazepine compound, stereoisomer thereof, pharmacologically acceptable salt thereof or hydrate thereof according to claim 1, wherein either or both of $R^2$ and $R^3$ are methoxyl group or $R^2$ and $R^3$ together form methylenedioxy group and $R^1$, $R^4$ and $R^5$ are each hydrogen atom.

3. The 5,11-Dihydrodibenzo[b,e][1,4]oxazepine compound, stereoisomer thereof, pharmacologically acceptable salt thereof or hydrate thereof according to claim 1, wherein $R^3$ is methoxyl group, and $R^1$, $R^2$, $R^4$ and $R^5$ are each hydrogen atom.

4. The 5,11-Dihydrodibenzo[b,e][1,4]oxazepine compound, stereoisomer thereof, pharmacologically acceptable salt thereof or hydrate thereof according to claim 1, wherein both of A and B-D are each CH$_2$.

5. The 5,11-Dihydrodibenzo[b,e][1,4]oxazepine compound, stereoisomer thereof, pharmacologically acceptable salt thereof or hydrate thereof according to claim 1, wherein the absolute configuration at the 3-position of the pyrrolidine ring in formula [Ib] is R-configuration.

6. A 5,11-Dihydrodibenzo[b,e][1,4]oxazepine compound of following formula [Ia], [Ib] or [Ic], a stereoisomer thereof, a pharmacologically acceptable salt thereof or a hydrate thereof:

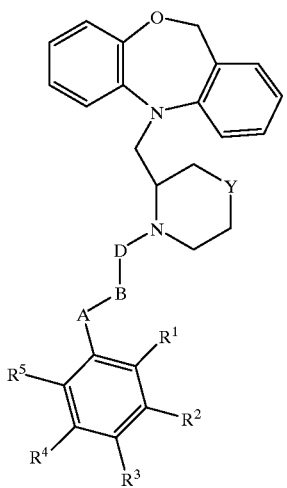

[Ia]

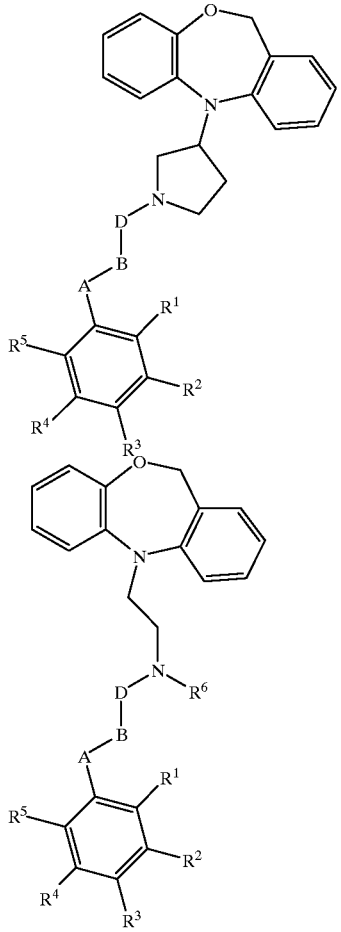

[Ib]

[Ic]

wherein one of $R^1$ through $R^5$ is amino group or a lower alkylamino group and the others are each hydrogen atom, $R^6$ represents hydrogen or a lower alkyl group, Y represents methylene group, oxygen atom, sulfur atom or an alkylamino group, A represents CH$^2$, CHOH, CO or O, B represents CH$_2$, CHOH or CO, or A-B represents CH=CH, and D represents CH$_2$, CH$_2$—CH$_2$ or CH$_2$—CH$_2$—CH$_2$, or B-D represents CH$_2$.

7. A 5,11-Dihydrodibenzo[b,e][1,4]oxazepine compound of following formula [Ia], [Ib] or [Ic], a stereoisomer thereof, a pharmacologically acceptable salt thereof or a hydrate thereof:

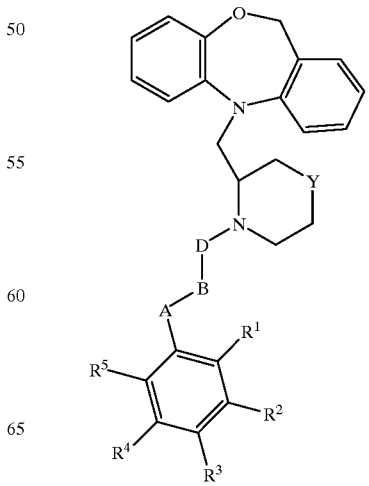

[Ia]

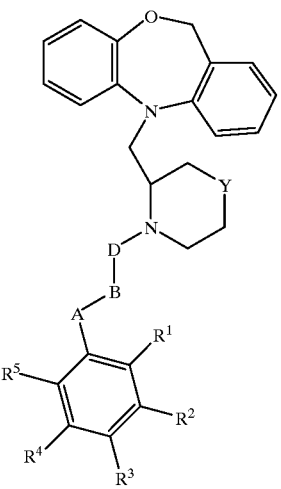

[Ia]

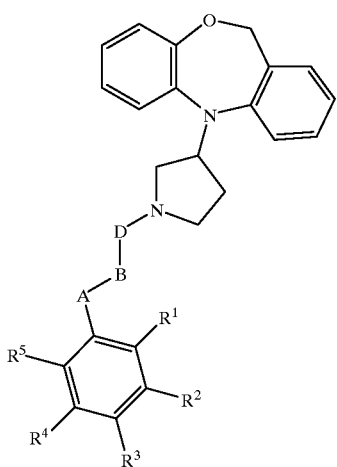

[Ib]

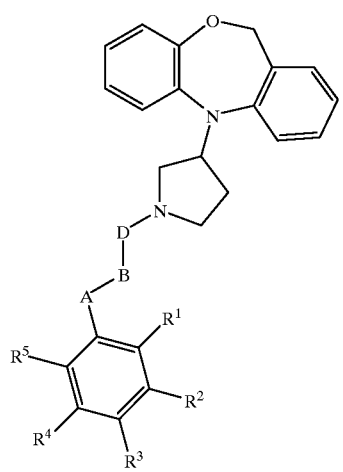

[Ib]

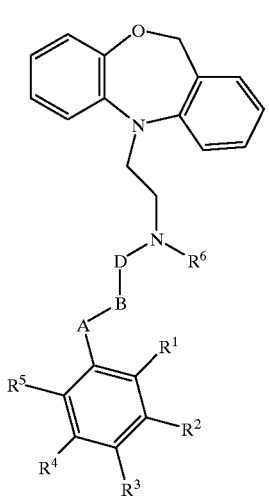

[Ic]

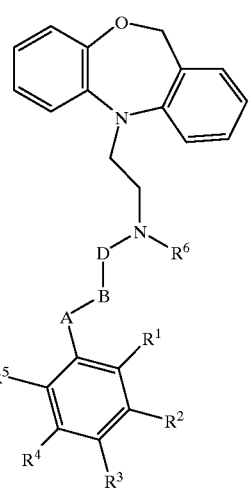

[Ic]

wherein $R^1$ to $R^5$ may be the same or different from each other and they each represent hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —$O(CH_2)_nO$— group (n being 1, 2 or 3), $R^6$ represents hydrogen or a lower alkyl group, Y represents methylene group, oxygen atom, sulfur atom or an alkylamino group, A represents $CH_2$, CHOH, CO or O, B represents $CH_2$, CHOH or CO, or A-B represents CH=CH, and D represents $CH_2$, $CH_2$—$CH_2$ or $CH_2$—$CH_2$—$CH_2$, or B-D represents $CH_2$, wherein Y in formula [Ia] is methylene.

8. A 5,11-Dihydrodibenzo[b,e][1,4]oxazepine compound of following formula [Ia], [Ib] or [Ic], a stereoisomer thereof, a pharmacologically acceptable salt thereof or a hydrate thereof:

wherein $R^1$ to $R^5$ may be the same or different from each other and they each represent hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —$O(CH_2)_nO$— group (n being 1, 2 or 3), $R^6$ represents hydrogen or a lower alkyl group, Y represents methylene group, oxygen atom, sulfur atom or an alkylamino group, A represents $CH_2$, CHOH, CO or O, B represents $CH_2$, CHOH or CO, or A-B represents CH=CH, and D represents $CH_2$, $CH_2$—$CH_2$ or $CH_2$—$CH_2$—$CH_2$, or B-D represents $CH_2$, wherein when Y in formula [Ia] is methylene, the absolute configuration at the 2-position of the piperidine ring in formula [Ia] is R-configuration and when Y is not methylene, the corresponding position of the nitrogen-containing 6-membered ring has a configuration equivalent thereto.

9. A 5,11-Dihydrodibenzo[b,e][1,4]oxazepine compound of following formula [Ia], [Ib] or [Ic], a stereoisomer thereof, a pharmacologically acceptable salt thereof or a hydrate thereof:

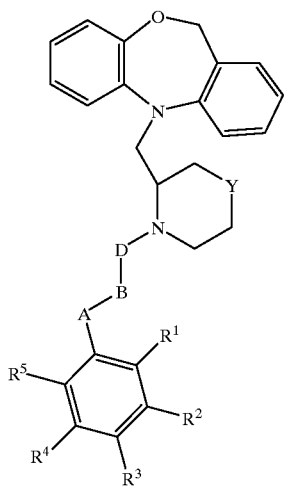

[Ia]

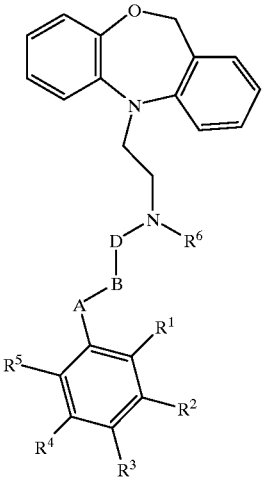

[Ic]

wherein $R^1$ to $R^5$ may be the same or different from each other and they each represent hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —$O(CH_2)_nO$— group (n being 1, 2 or 3), $R^6$ represents hydrogen or a lower alkyl group, Y represents methylene group, oxygen atom, sulfur atom or an alkylamino group, A represents $CH_2$, CHOH, CO or O, B represents $CH_2$, CHOH or CO, or A-B represents CH=CH, and D represents $CH_2$, $CH_2$—$CH_2$ or $CH_2$—$CH_2$—$CH_2$, or B-D represents $CH_2$, wherein $R^6$ in formula [Ic] is a lower alkyl group having 1 to 3 carbon atoms.

10. A pharmaceutical composition comprising a 5,11-dihydrodibenzo[b,e][1,4]oxazepine compound, a stereoisomer thereof, a pharmacologically acceptable salt thereof or a hydrate thereof according to claim 1.

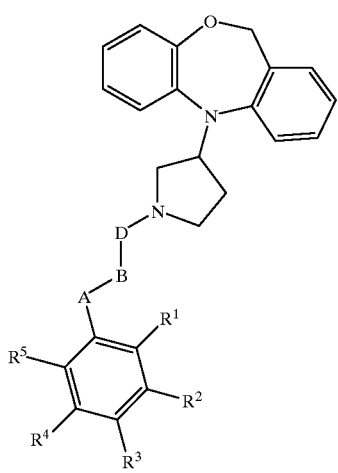

[Ib]

11. A method for treating an intestinal disease or disorder of the gastrointestinal tract comprising administering an effective amount of a 5,11-dihydrodibenzo[b,e][1,4] oxazepine compound, a stereoisomer thereof, a pharmacologically acceptable salt thereof or a hydrate thereof according to claim 1, to a subject in need thereof.

12. The method of claim 11, wherein said disease or disorder is associated with an abnormal motor function of the gastrointestinal tract.

13. The method of claim 11, wherein said disease is irritable bowel syndrome.

14. A process for making Compound [Ia], comprising reacting a compound of formula [IIa] with a compound of formula [IIIa] according to the following reaction scheme:

15. A process for making Compound [Ib], comprising reacting a compound of formula [IIb] with a compound of formula [IIIb] according to the following reaction scheme:

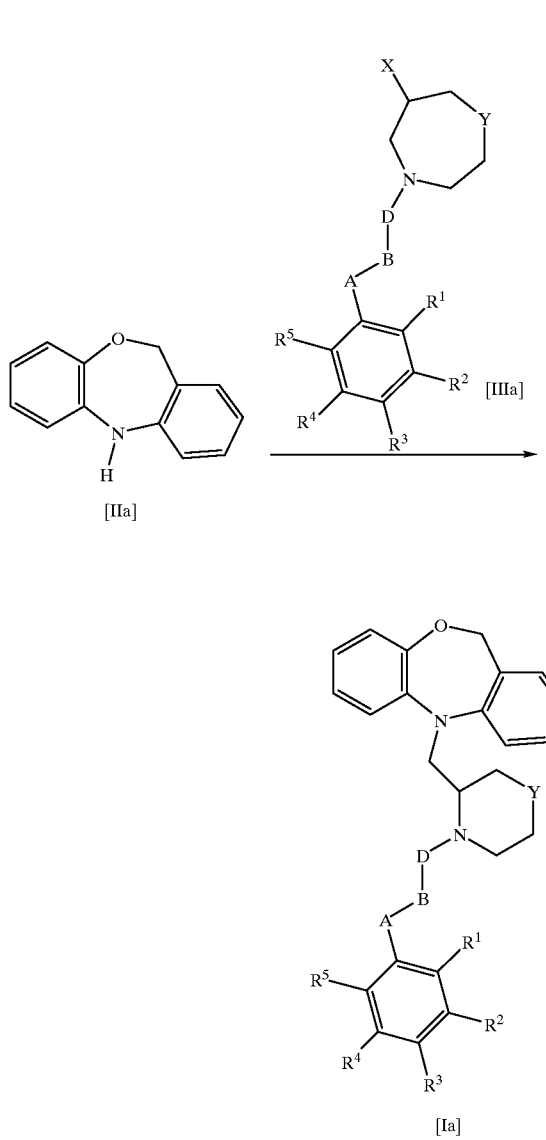

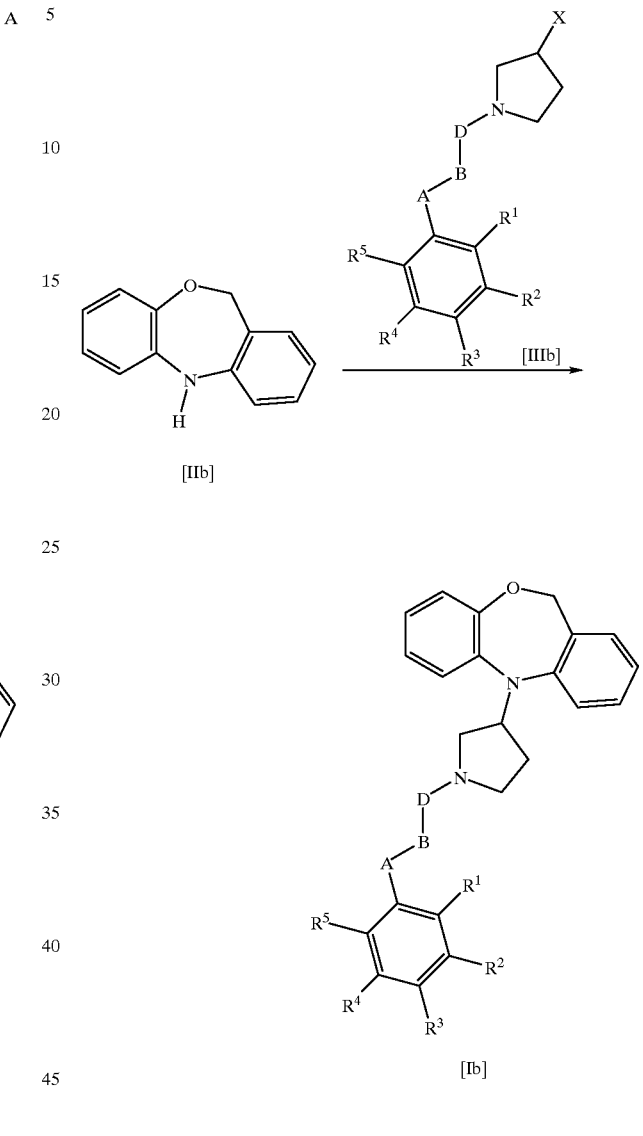

wherein $R^1$ to $R^5$ may be the same or different and each independently represents a hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —O(CH$_2$)$_n$O— group (n being 1, 2 or 3), Y represents methylene group, oxygen atom, sulfur atom or an alkylamino group, A represents CH$_2$, CHOH, CO or O, B represents CH$_2$, CHOH or CO, or A-B represents CH=CH, and D represents CH$_2$, CH$_2$—CH$_2$ or CH$_2$—CH$_2$—CH$_2$, or B-D represents CH$_2$, and wherein X is selected from the group consisting of chlorine atom, bromine atom, and iodine atom.

wherein $R^1$ to $R^5$ may be the same or different and each independently represents a hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —O(CH$_2$)$_n$O— group (n being 1, 2 or 3), A represents CH$_2$, CHOH, CO or O, B represents CH$_2$, CHOH or CO, or A-B represents CH=CH, and D represents CH$_2$, CH$_2$—CH$_2$ or CH$_2$—CH$_2$—CH$_2$, or B-D represents CH$_2$ and wherein X represents a leaving group.

16. The process of claim 15, wherein X is selected from the group consisting of halogen atoms, a tosyloxy group, and a mesyloxy group.

17. A process for making Compound [Ic] comprising the following reaction scheme:

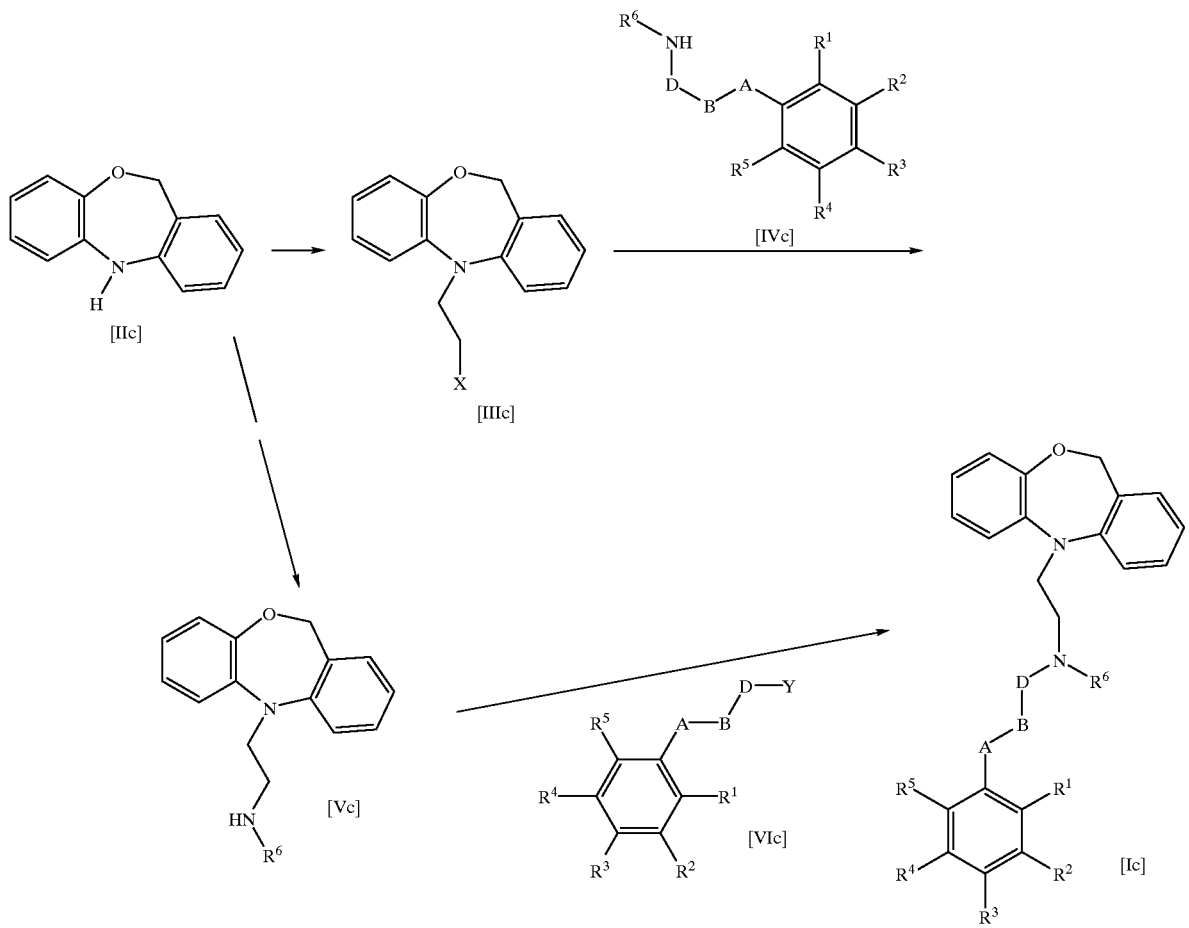

wherein $R^1$ to $R^5$ may be the same or different and each independently represent a hydrogen atom, a halogen atom, cyano group, hydroxyl group, a lower alkyl group, a lower alkoxyl group, amino group or a lower alkylamino group, or $R^1$ and $R^2$, $R^2$ and $R^3$, $R^3$ and $R^4$ or $R^4$ and $R^5$ together represent —O(CH$_2$)$_n$O— group (n being 1, 2 or 3), $R^6$ represents hydrogen or a lower alkyl group, A represents CH$_2$, CHOH, CO or O, B represents CH$_2$, CHOH or CO, or A-B represents CH=CH, and D represents CH$_2$, CH$_2$—CH$_2$ or CH$_2$—CH$_2$—CH$_2$, or B-D represents CH$_2$ and wherein X and Y each represent a leaving group.

18. The process of claim 17, wherein X and Y are selected from the group consisting of halogen atoms, a tosyloxy group, and a mesyloxy group.

* * * * *